(12) United States Patent
Presz, Jr. et al.

(10) Patent No.: US 9,533,241 B2
(45) Date of Patent: *Jan. 3, 2017

(54) METHODS AND APPARATUS FOR PARTICLE AGGREGATION USING ACOUSTIC STANDING WAVES

(71) Applicant: FloDesign Sonics, Inc., Wilbraham, MA (US)

(72) Inventors: Walter M. Presz, Jr., Wilbraham, MA (US); Kedar Chitale, West Hartford, CT (US); Bart Lipkens, Hampden, MA (US)

(73) Assignee: FloDesign Sonics, Inc., Wilbraham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/080,354

(22) Filed: Mar. 24, 2016

(65) Prior Publication Data
US 2016/0279540 A1    Sep. 29, 2016

Related U.S. Application Data

(60) Provisional application No. 62/162,831, filed on May 18, 2015, provisional application No. 62/137,795, filed on Mar. 24, 2015.

(51) Int. Cl.
*B01D 41/00* (2006.01)
*B01D 21/28* (2006.01)
(Continued)

(52) U.S. Cl.
CPC .............. *B01D 21/283* (2013.01); *C02F 1/36* (2013.01); *C12M 47/02* (2013.01)

(58) Field of Classification Search
CPC ..................... B01D 21/283; B01D 2021/0081; B01D 43/00; B01J 19/10; C02F 1/36
See application file for complete search history.

(56) References Cited

U.S. PATENT DOCUMENTS 5,085,783 A * 2/1992 Feke .................... B01D 21/283
                                                          210/243
5,164,094 A * 11/1992 Stuckart .............. B01D 21/283
                                                          204/157.15

(Continued)

FOREIGN PATENT DOCUMENTS

WO    WO 2004/079716 A1    9/2004
WO    WO 2014/124306 A1    8/2014

OTHER PUBLICATIONS

Ilinskii et al.; Acoustic Radiation Force on a Sphere in Tissue; AIP Conference Proceedings; 2012.
(Continued)

*Primary Examiner* — Walter D Griffin
*Assistant Examiner* — Cameron Allen
(74) *Attorney, Agent, or Firm* — Richard M. Klein; Fay Sharpe LLP

(57) ABSTRACT

Devices for separating materials from a host fluid are disclosed. The devices include an acoustic chamber having an inlet and an outlet. An ultrasonic transducer and reflector create a multi-dimensional acoustic standing wave in the acoustic chamber that traps the materials and permits a continuous separation of the materials from the host fluid. The materials and the host fluid can thus be separately collected. Multiple sets of trapping lines are generated by the acoustic standing wave, and the transducer is oriented to minimize cross-sectional area for straight vertical channels between the trapping lines.

20 Claims, 34 Drawing Sheets

(51) Int. Cl.
    *C02F 1/36*    (2006.01)
    *C12M 1/00*    (2006.01)

(56)  References Cited

U.S. PATENT DOCUMENTS

| | | | | |
|---|---|---|---|---|
| 2004/0112841 A1* | 6/2004 | Scott | ............. | B01J 8/005 |
| | | | | 210/748.05 |
| 2010/0206818 A1* | 8/2010 | Leong | ............. | B01D 21/283 |
| | | | | 210/748.05 |
| 2014/0319077 A1 | 10/2014 | Lipkens et al. | | |

OTHER PUBLICATIONS

International Search Report and Written Opinion for International Application No. PCT/US2016/024082 dated Jun. 27, 2016.

* cited by examiner

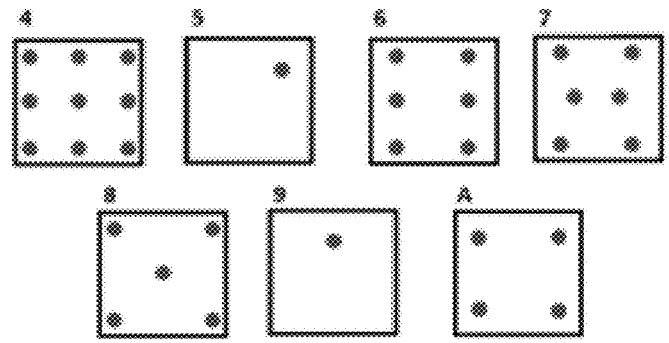
Figure 14A
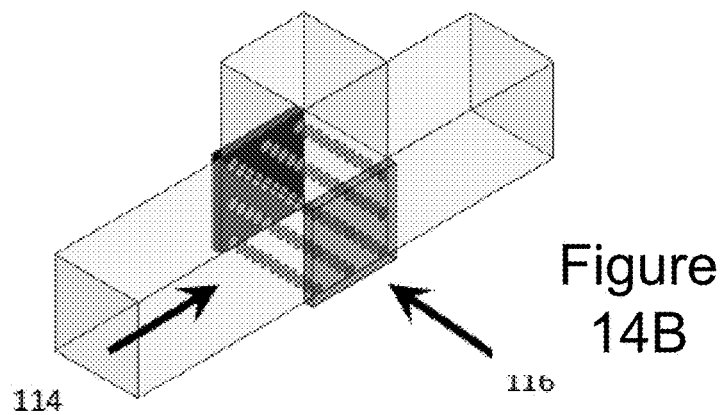
Figure 14B
Figure 14C
Figure 14D
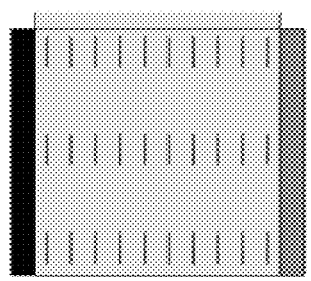
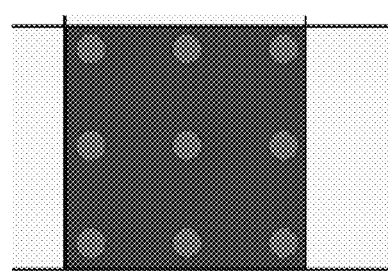

$$F_{DF} = F_{DG}$$

$$F_{DF} = C_D \frac{1}{2}\rho V_D^2 HD$$

$$F_{DG} = \frac{\varphi}{2}(\rho_P - \rho_F)g\frac{\pi D^2}{4}H$$

$$C_D \frac{1}{2}\rho V_D^2 \cancel{HD} = \frac{\varphi}{2}(\rho_P - \rho_F)g\frac{\pi D^2}{4}H$$

$$C_D V_D^2 = \varphi\left(\frac{\rho_P}{\rho_F} - 1\right)g\frac{\pi D}{4}$$

METHODS AND APPARATUS FOR PARTICLE AGGREGATION USING ACOUSTIC STANDING WAVES

CROSS-REFERENCE TO RELATED APPLICATIONS

This application claims priority to U.S. Provisional Patent Application Ser. No. 62/162,831, filed on May 18, 2015; and to U.S. Provisional Patent Application Ser. No. 62/137,795, filed on Mar. 24, 2015, the disclosures of which are hereby fully incorporated by reference in their entireties.

BACKGROUND

When particles are entrained or dispersed in a flowing fluid, aggregation of the particles to form larger clumps is typically due to some attraction or adhesion between the particles or the addition of a flocculating agent that aids in attracting and aggregating the particles. Attractive forces between the particles may be ionic or physical entanglement. Some flocculating agents, such as chitosan, may also be directly attractive to the particles and thus form clumps of particles in the fluid medium.

Typically, after the clumps of particles are formed in the fluid medium, a physical filtration process is utilized to separate the aggregated, agglomerated, flocculated or otherwise process-formed particle clumps. If this is a filter separation process, the physical filter media and the clumps of particles that have been separated from the fluid media are typically discarded, thus creating additional waste and increasing costs. Also, with the use of this physical filtration process, the yield of the filtrate is lessened, as some of it is used to saturate the filtering material. Further, as the filter fills up, filtration capacity is reduced, and using such filters requires periodic stopping to remove the filter and obtain the particles trapped thereon.

An example of this type of filtration is the filtering of a bioreactor to separate the cells and cell debris from the expressed products of the cells, such as monoclonal antibodies and recombinant proteins. Many times, this entails the use of a diatomaceous earth (DE) filter. The DE filters become filled quickly with the cellular waste from the bioreactor during the filtration process. This decreases the flux rate, the ability of the filter to trap materials and allow the fluid to pass through the filter, and increases the pressure differential between the material to be filtered and the post-filter material. As a result, some of the product from the bioreactor (monoclonal antibodies and recombinant proteins) is lost, thus decreasing the yield of the bioreactor. Also, any high pressure differential generated by the filter blockage can generate product damage.

Thus, methods are sought where continuous filtration may be carried out with little or no loss of the expressed monoclonal antibodies and recombinant proteins while separating most or all of the cells and cell debris that are in the bioreactor fluid. Such continuous methods would also be useful in other filtration applications such as the filtering of oil from water, components from blood, tailings from water in tailing ponds, and, generally, particles from a fluid stream and immiscible or emulsified fluids from a fluid stream.

Acoustophoresis is the separation of particles and secondary fluids from a primary or host fluid using high intensity acoustic standing waves, and without the use of membranes or physical size exclusion filters. It has been known that high intensity standing waves of sound can exert forces on particles in a fluid when there is a differential in both density and/or compressibility, otherwise known as the acoustic contrast factor. The pressure profile in a standing wave contains areas of local minimum pressure amplitudes at its nodes and local maxima at its anti-nodes. Depending on the density and compressibility of the particles, they will be trapped at the nodes or anti-nodes of the standing wave. Generally, the higher the frequency of the standing wave, the smaller the particles that can be trapped due the pressure of the standing wave.

At the MEMS scale, the conventional acoustophoresis systems rely on using half or quarter wavelength acoustic chambers, which at frequencies of a few megahertz are typically less than a millimeter in thickness, and operate at very slow flow rates (e.g., µL/min). Such systems are not scalable since they benefit from extremely low Reynolds number, laminar flow operation, and require minimal fluid dynamic optimization.

At the macro-scale, planar acoustic standing waves have been used to accomplish this separation process. However, a single planar wave tends to trap the particles or secondary fluid in a manner such that they can only be separated from the primary fluid by turning off the planar standing wave. This does not allow for continuous operation. Also, the amount of power that is needed to generate the acoustic planar standing wave tends to heat the primary fluid through waste energy.

Conventional acoustophoresis devices have thus had limited efficacy due to several factors including heat generation, use of planar standing waves, limits on fluid flow, and the inability to capture different types of materials. It would therefore be desirable to provide systems and methods of generating optimized particle clusters to improve gravity separation and collection efficiency. Improved acoustophoresis devices using improved fluid dynamics would also be desirable, so the acoustophoresis can be a continuous process.

BRIEF DESCRIPTION

The present disclosure relates, in various embodiments, to acoustophoretic systems with improved fluid dynamics that can be used to improve the separation of particles from a particle/fluid mixture. More particularly, the systems and methods disclosed herein use reduced frequencies to enhance particle concentration in optimal shapes to improve their separation by gravity and subsequent collection. The systems include an acoustic chamber containing an ultrasonic transducer and reflector that set up a multi-dimensional acoustic standing wave.

The systems described herein can use a substantially vertical flow path of the mixture through the acoustic chamber in order to improve separation of particles/secondary fluid from a primary fluid using fluid dynamics. The vertical flow path reduces velocity non-uniformities in the acoustic chamber resulting from gravity forces. In additional systems, a dump diffuser is used to make the incoming flow more uniform, so that the efficiency of the acoustophoretic system is maximized. However, the present system is not limited to vertical flow.

Disclosed herein are acoustophoresis devices comprising: a housing having a sidewall that defines an acoustic chamber; at least one outlet in the acoustic chamber; at least one inlet in the acoustic chamber; and at least one ultrasonic transducer located on the sidewall of the acoustic chamber and at least one reflector located on the sidewall of the housing opposite the at least one ultrasonic transducer, the transducer including a piezoelectric material driven by a voltage signal to create a multi-dimensional acoustic standing wave in the acoustic chamber.

Also disclosed are methods of separating a host fluid from a second fluid or particulate, the methods comprising: flowing a mixture of the host fluid and the second fluid or particulate through an acoustophoresis device in a uniform fashion, the device comprising: a housing having a sidewall that defines an acoustic chamber; at least one outlet from the acoustic chamber; at least one inlet to the acoustic chamber; and at least one ultrasonic transducer located on the sidewall of the acoustic chamber and at least one reflector located on the sidewall of the housing opposite the at least one ultrasonic transducer, the transducer including a piezoelectric material driven by a voltage signal to create a multi-dimensional acoustic standing wave in the acoustic chamber; and trapping smaller particles of the second fluid or particulate in the acoustic standing wave to generate particle clusters that subsequently fall into the at least one lower outlet; wherein the acoustic standing wave has a ratio of lateral radiation force to axial radiation force of the same order of magnitude.

The piezoelectric material may be operated to produce a single trapping line, or to produce a set of vertically-staggered trapping lines. The at least one ultrasonic transducer may be driven at a frequency of about 0.5 MHz to about 4 MHz, or at a frequency below about 1.5 MHz.

In particular constructions, the at least one inlet is part of a dump diffuser. The at least one inlet may be located at a height between 5% and 75% of a height of the acoustic chamber. The at least one inlet may be in the shape of holes or slots that provide an initial flow direction parallel to the multi-dimensional acoustic standing wave generated by the at least one ultrasonic transducer. The device may include a shallow wall below the at least one inlet and leading to the at least one outlet, wherein the shallow wall has an angle of 60° or less relative to a horizontal plane.

The acoustophoresis device may be reflectionally symmetrical through a vertical plane. The at least one inlet may include a plurality of inlets located about the housing, such that the inflow of the mixture into the acoustic chamber is uniform and symmetrical.

In particular embodiments, the piezoelectric material is oriented to minimize cross-sectional area for straight vertical channels between trapping lines generated by the acoustic standing wave. The mixture of the host fluid and the second fluid or particulate is flowed through the acoustophoresis device at a rate of at least 4.65 mL/minute per cm².

The particulate may be Chinese hamster ovary (CHO) cells, NS0 hybridoma cells, baby hamster kidney (BHK) cells, or human cells, T cells, B cells, NK cells, algae, bacteria, viruses, or microcarriers.

Also disclosed in various embodiments herein are acoustophoresis devices comprising: a housing having a sidewall that defines an acoustic chamber; and at least one ultrasonic transducer located on the sidewall of the acoustic chamber and at least one reflector located on the sidewall of the housing opposite the at least one ultrasonic transducer, the transducer including a piezoelectric material driven by a voltage signal to create a multi-dimensional acoustic standing wave in the acoustic chamber, resulting in a set of trapping lines in the acoustic chamber, the transducer being oriented to minimize cross-sectional area for straight vertical channels between the trapping lines. This can be done as described herein.

Also disclosed are methods of separating a host fluid from a second fluid or particulate, the method comprising: flowing a mixture of the host fluid and the second fluid or particulate through an acoustophoresis device in a uniform fashion, the device comprising: a housing having a sidewall that defines an acoustic chamber; at least one ultrasonic transducer located on the sidewall of the acoustic chamber and at least one reflector located on the sidewall of the housing opposite the at least one ultrasonic transducer, the transducer including a piezoelectric material driven by a voltage signal to create a multi-dimensional acoustic standing wave in the acoustic chamber, resulting in a set of trapping lines in the acoustic chamber, the transducer being oriented to minimize cross-sectional area for straight vertical channels between the trapping lines; and capturing smaller particles of the second fluid or particulate in the trapping lines to cluster and continuously gravity separate the second fluid or particulate from the host fluid.

The at least one ultrasonic transducer may be driven at or below a frequency of about 1.5 MHz, and in particular at a frequency of about 1 MHz. The particulate may be Chinese hamster ovary (CHO) cells, NS0 hybridoma cells, baby hamster kidney (BHK) cells, or human cells, T cells, B cells, NK cells, algae, bacteria, viruses, or microcarriers.

These and other non-limiting characteristics are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

FIG. 14A illustrates the trapping line configurations for seven peak amplitudes of an ultrasonic transducer of the present disclosure. FIG. 14B is a perspective view illustrating a separator of the present disclosure. The fluid flow direction and the trapping lines are shown. FIG. 14C is a view from the fluid inlet along the fluid flow direction (arrow 114) of FIG. 14B, showing the trapping nodes of the standing wave where particles would be captured. FIG. 14D is a view taken through the transducers face at the trapping line configurations, along arrow 116 as shown in FIG. 14B.

FIG. 19 shows the calculation of the cluster terminal velocity of a cylindrical cluster from the cluster drag and gravitational forces.

Figure 1:
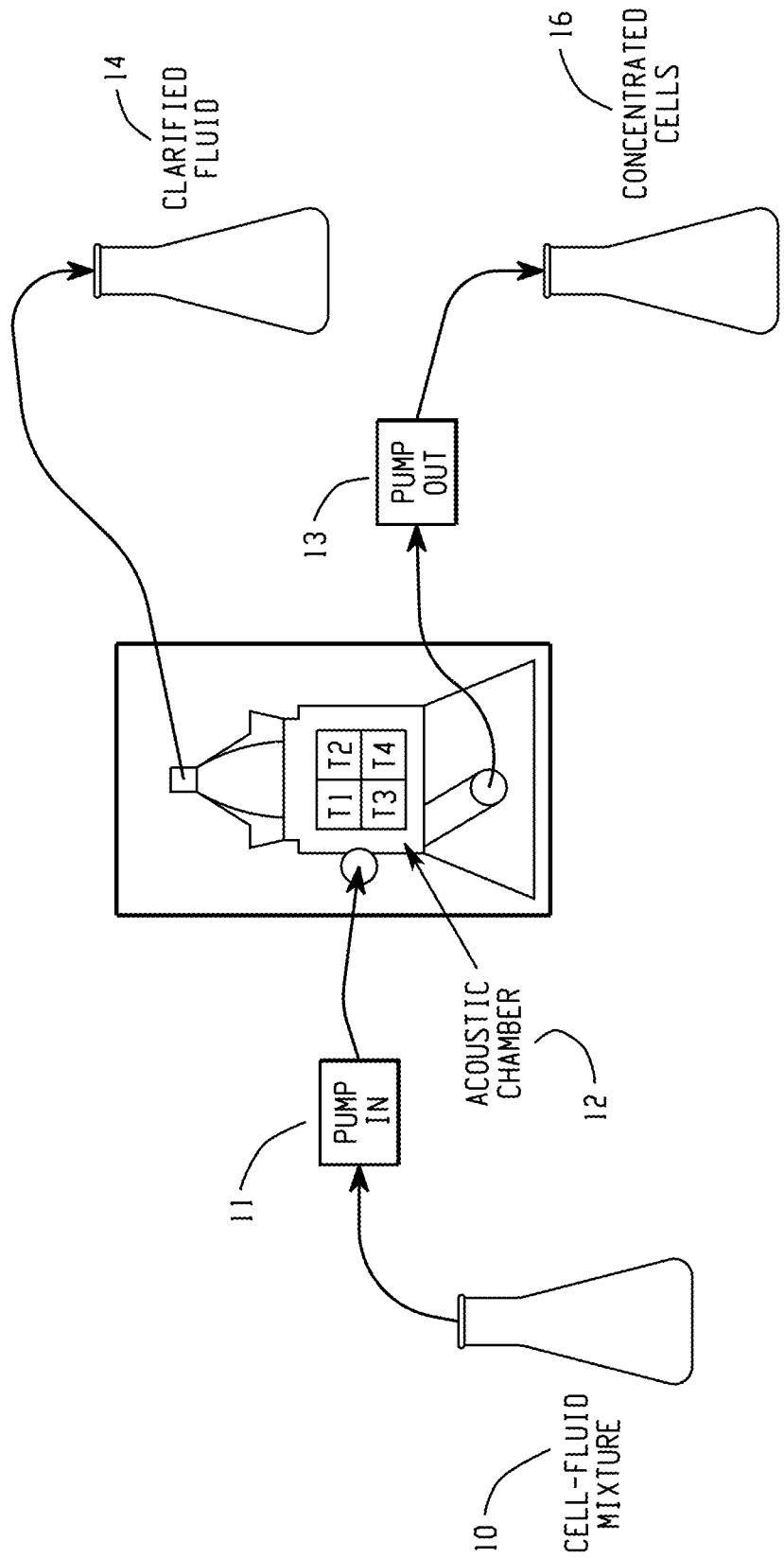
FIG. 1 illustrates an exemplary acoustophoretic separation system in which a cell-fluid mixture is clarified, such that clarified fluid and concentrated cells are removed therefrom in different containers.

FIG. 20 is a graph showing the predicted cylindrical cluster drop velocity versus non-dimensional cluster diameter (D/λ) where lambda (λ) is the axial wavelength of the standing wave. The y-axis runs from 0 to 1.6 in intervals of 0.2. The x-axis runs from 0 to 3.5 in intervals of 0.5.

FIG. 21 is the graph of FIG. 20, showing the predicted cluster drop velocity for a cluster diameter D/λ=1.62 is approximately 1 cm/sec or 0.01 m/sec.

FIG. 22 is a graph showing particle collection flowrate in mL/min versus non-dimensional cluster diameter (D/λ) for the system of FIG. 20. The y-axis runs from 0 to 6 in intervals of 1. The x-axis runs from 0 to 3.5 in intervals of 0.5.

FIG. 23 is a graph of clarification performance (%) versus cluster particle flowrate (mL/min) for the system of FIG. 20. The y-axis runs from 0 to 100 in intervals of 10. The x-axis runs from 0 to 90 in intervals of 10.

FIG. 24 is a graph showing predicted system particle collection potential (mL/min) versus non-dimensional cluster diameter (D/λ) for the system of FIG. 20. The y-axis runs from 0 to 16 in intervals of 2. The x-axis runs from 0 to 0.0045 in intervals of 0.0005.

FIG. 25 is a graph showing the predicted cluster drop velocity (cm/sec) versus lateral-to-axial radiation force ratio ($F_L/F_A$) for the system of FIG. 20. The y-axis runs from 0 to 1.6 in intervals of 0.2. The x-axis runs from 0 to 1.2 in intervals of 0.2.

FIG. 26 is a COMSOL simulation showing the lateral-to-axial radiation force ratio ($F_L/F_A$) versus frequency (MHz) for many different operating modes of a crystal, including with different structures. The y-axis runs from 0 to 0.35 in intervals of 0.5. The x-axis runs from 2.2 to 2.3 in intervals of 0.01.

FIG. 27 is a graph showing predicted cluster drop velocity (cm/sec) versus lateral-to-axial radiation force ratio ($F_L/F_A$) for both 1 MHz and 2 MHz frequencies. The y-axis runs from 0 to 1.8 in intervals of 0.2. The x-axis runs from 0 to 1.2 in intervals of 0.2.

FIG. 28 is a graph plotting the predicted cluster drop velocity (cm/sec) of FIG. 27 versus non-dimensional cluster diameter (D/λ). The y-axis runs from 0 to 1.8 in intervals of 0.2. The x-axis runs from 0 to 3.5 in intervals of 0.5.

FIG. 29 is a graph showing the particle collection flowrate (mL/min) of FIG. 27 versus non-dimensional cluster diameter (D/λ). The y-axis runs from 0 to 20 in intervals of 2. The x-axis runs from 0 to 3.5 in intervals of 0.5.

FIG. 30 is an illustration of clusters with large diameters bleeding into clusters below them, resulting in high concentrate particle collection.

FIG. 31 shows a diagram of nine trapping lines with large channels between them, with the arrows representing leakage pathways resulting in little or no lateral forces on the clusters in the trapping lines.

FIG. 32A illustrates an ultrasonic transducer of the present disclosure that has a crystal in the shape of an irregular polygon, such that long leakage pathways are not formed.

FIG. 32B illustrates another ultrasonic transducer according to the present disclosure where the transducer is tilted, such that long leakage pathways are not formed.

FIG. 33 is a cross-sectional diagram of an acoustophoretic device including two dump diffusers used to make the inflow more uniform.

FIG. 34 is a perspective view of an exemplary dump diffuser.

FIG. 35 is a side view of the exemplary dump diffuser of FIG. 34.

DETAILED DESCRIPTION

The present disclosure may be understood more readily by reference to the following detailed description of desired embodiments and the examples included therein. In the following specification and the claims which follow, reference will be made to a number of terms which shall be defined to have the following meanings.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

The term "comprising" is used herein as requiring the presence of the named component and allowing the presence of other components. The term "comprising" should be construed to include the term "consisting of", which allows the presence of only the named component, along with any impurities that might result from the manufacture of the named component.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values). The endpoints of the ranges and any values disclosed herein are not limited to the precise range or value; they are sufficiently imprecise to include values approximating these ranges and/or values.

The modifier "about" used in connection with a quantity is inclusive of the stated value and has the meaning dictated by the context. When used in the context of a range, the modifier "about" should also be considered as disclosing the range defined by the absolute values of the two endpoints. For example, the range of "from about 2 to about 10" also discloses the range "from 2 to 10." The term "about" may refer to plus or minus 10% of the indicated number. For example, "about 10%" may indicate a range of 9% to 11%, and "about 1" may mean from 0.9-1.1.

It should be noted that many of the terms used herein are relative terms. For example, the terms "upper" and "lower" are relative to each other in location, i.e. an upper component is located at a higher elevation than a lower component in a given orientation, but these terms can change if the device is flipped. The terms "inlet" and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows through various components, i.e. the flow fluids through an upstream component prior to flowing through the downstream component. It should be noted that in a loop, a first component can be described as being both upstream of and downstream of a second component.

The terms "horizontal" and "vertical" are used to indicate direction relative to an absolute reference, i.e. ground level. However, these terms should not be construed to require structures to be absolutely parallel or absolutely perpendicular to each other. For example, a first vertical structure and a second vertical structure are not necessarily parallel to each other. The terms "top" and "bottom" or "base" are used to refer to surfaces where the top is always higher than the bottom/base relative to an absolute reference, i.e. the surface of the earth. The terms "upwards" and "downwards" are also relative to an absolute reference; upwards is always against the gravity of the earth.

The term "parallel" should be construed in its lay sense of two surfaces that maintain a generally constant distance between them, and not in the strict mathematical sense that such surfaces will never intersect when extended to infinity.

The present application refers to "the same order of magnitude." Two numbers are of the same order of magnitude if the quotient of the larger number divided by the smaller number is a value less than 10.

The present disclosure relates to acoustophoretic devices that employ multi-dimensional ultrasonic acoustic standing waves to trap, i.e., hold stationary, particles or a secondary fluid in a host fluid stream. The multi-dimensional acoustic standing wave generates tightly packed clusters of suspended fluid or particulate which continuously drop out or rise out of a flowing fluid mixture due to gravity forces. These systems can operate at high flowrates that require significant fluid dynamic optimization to function properly.

FIG. 1 is a broad overview of an acoustic wave separator system. A mixture 10 of a host fluid and a secondary phase (e.g. particles, cells, or a second different fluid) is sent via a pump 11 into an acoustic chamber 12. Here, the mixture is a cell-fluid mixture. In the acoustic chamber, the secondary phase is concentrated out of the host fluid. The concentrated cells 16 are sent by another pump 13 to be collected. The host fluid, which is more clarified due to the removal of the concentrated cells, is separately collected (indicated by reference numeral 14). Generally speaking, the acoustic chamber has at least one inlet and at least one outlet.

Figure 2:
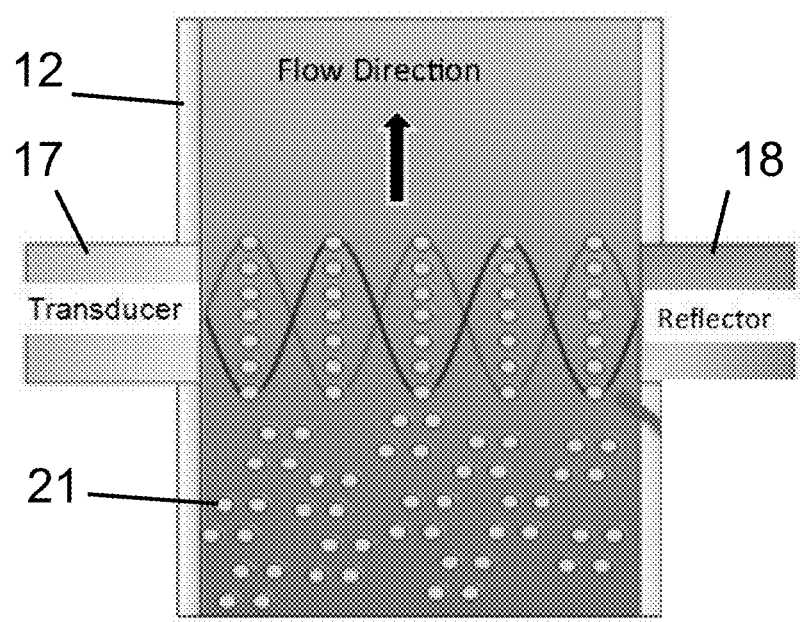
FIG. 2 illustrates standing acoustic wave(s) generated by an ultrasonic transducer and a reflector perpendicular to a direction of flow.

The acoustic chamber operates as shown in FIG. 2. One or more multi-dimensional acoustic standing waves are created between an ultrasonic transducer 17 and a reflector 18. The particles or secondary fluid 21 will collect, agglomerate, aggregate, clump, or coalesce at the nodes or anti-nodes of the multi-dimensional acoustic standing wave, depending on the particles' or secondary fluid's acoustic contrast factor relative to the host fluid, forming clusters that eventually fall out of the multi-dimensional acoustic standing wave when the clusters have grown to a size large enough to overcome the holding force of the multi-dimensional acoustic standing wave (e.g. by coalescence or agglomeration). For fluids/particles that are less dense than the host fluid (such as the cells of FIG. 1), the clusters sink to the bottom and can be collected separately from the clarified host fluid. For fluids/particles that are more dense than the host fluid, the buoyant clusters float upwards and can be collected. This is an important distinction from previous approaches where particle trajectories were merely altered by the effect of the acoustic radiation force.

The scattering of the acoustic field off the particles results in a three dimensional acoustic radiation force, which acts as a three-dimensional trapping field. The acoustic radiation force is proportional to the particle volume (e.g. the cube of the radius) when the particle is small relative to the wavelength. It is proportional to frequency and the acoustic contrast factor. It also scales with acoustic energy (e.g. the square of the acoustic pressure amplitude). When the acoustic radiation force exerted on the particles is stronger than the combined effect of fluid drag force and buoyancy and gravitational force, the particles are trapped within the acoustic standing wave field. This results in concentration, agglomeration and/or coalescence of the trapped particles. Relatively large solids of one material can thus be separated from smaller particles of a different material, the same material, and/or the host fluid through enhanced gravitational separation.

The multi-dimensional standing wave generates acoustic radiation forces in both the axial direction (i.e., in the direction of the standing wave, between the transducer and the reflector, perpendicular to the flow direction) and the lateral direction (i.e., in the flow direction). As the mixture flows through the acoustic chamber, particles in suspension experience a strong axial force component in the direction of the standing wave. Since this acoustic force is perpendicular to the flow direction and the drag force, it quickly moves the particles to pressure nodal planes or anti-nodal planes, depending on the contrast factor of the particle. The lateral acoustic radiation force then acts to move the concentrated particles towards the center of each planar node, resulting in agglomeration or clumping. The lateral acoustic radiation force component has to overcome fluid drag for such clumps of particles to continually grow and then drop out of the mixture due to gravity. Therefore, both the drop in drag per particle as the particle cluster increases in size, as well as the drop in acoustic radiation force per particle as the particle cluster grows in size, must be considered for the acoustic separator device to work effectively. In the present disclosure, the lateral force component and the axial force component of the multi-dimensional acoustic standing wave are of the same order of magnitude. In some particular embodiments, the ratio of the lateral force component to the axial force component is about 0.5 or less. In this regard, it is noted that in a multi-dimensional acoustic standing wave, the axial force is stronger than the lateral force, but the lateral force of a multi-dimensional acoustic standing wave is much higher than the lateral force of a planar standing wave, usually by two orders of magnitude or more.

In optimizing the operation of the systems of the present disclosure, consideration of particle drag and acoustic radiation force effects is necessary. At low Reynolds numbers of less than 10, laminar flow dominates, and viscous forces are much stronger than inertial forces.

As the particles are trapped by the multi-dimensional ultrasonic acoustic standing wave, they begin to aggregate and form a clump of particles. The drag on this clump of particles is a function of the geometry of the clump and is not merely the sum of the drag of the individual particles that make up the clump.

For laminar flow, the Navier Stokes equation is expressed as:

$$\rho\left(\frac{\partial V}{\partial t} + (V \cdot \nabla)V\right) = -\nabla P + \mu \nabla^2 V$$

where $$\frac{\partial V}{\partial t}$$

represents unsteady motion, $(V \cdot \nabla)V$ represents inertial motion, $-\nabla P$ represents pressure motion, and $\mu \nabla^2 V$ represents viscous motion.

For low Reynolds numbers, the unsteady motion and inertial motion terms can be ignored (i.e. set equal to zero), and the equation can be simplified to:

$$\nabla P = \mu \nabla^2 V$$

For a particle of diameter a, the following equations hold:

$$\nabla P \propto \mu \frac{V}{a}$$

$$F = 6\pi\mu aV$$

where P is pressure, $\mu$ is the dynamic viscosity, a is the particle diameter, V is the flow velocity, and F is the Stoke's drag.

Figure 3:
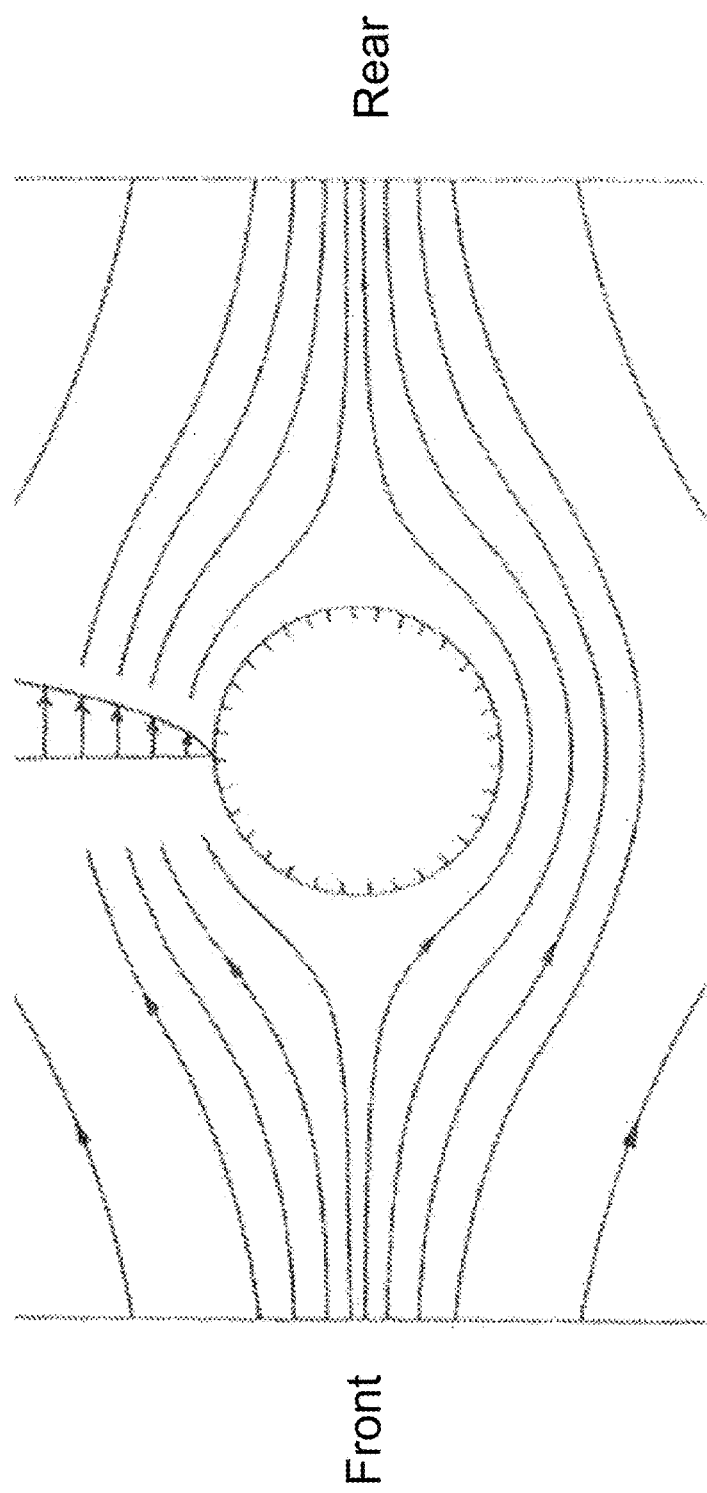
FIG. 3 illustrates the Stokes pressure distribution of a spherical particle cluster.

FIG. 3 is an illustration of fluid flow around a particle and the shear forces resulting therefrom. Fluid flow is from the left-hand side of the figure, and the left-hand side of the figure is also considered the front of the particle. The fluid flows into the front face of the particle, increasing pressure. The shear forces then drag the flow around the body while continually decreasing pressure. Finally, the shear forces drag the fluid away from the back face region lowering pressure. That is, the shear forces generally drag the fluid over the body.

Figure 4:
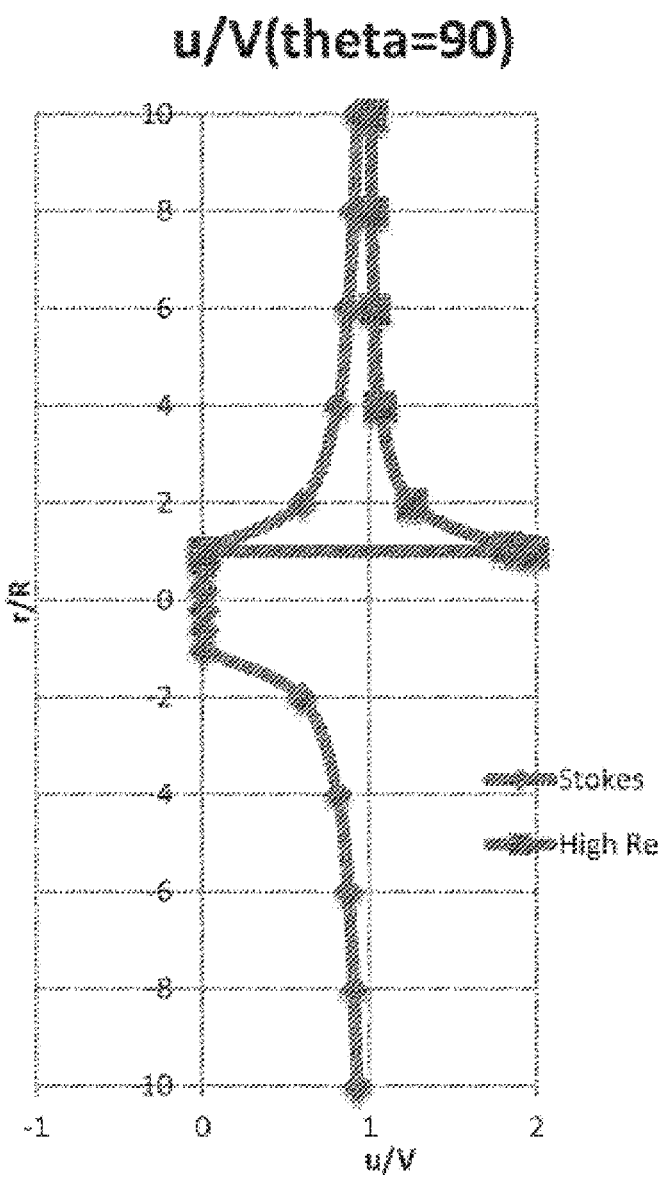
FIG. 4 is a graph illustrating the normalized flow velocity profile (u/V) over a sphere at the 90° location from the flow axis in terms of radiuses from the particle (r/R). The y-axis is r/R, and runs from −10 (at the bottom) to +10 (at the top) in intervals of 2. The x-axis runs from −1 to +2 in intervals of 1.

FIG. 4 is a graph illustrating the difference between Stokes flow (i.e. low Reynolds number, abbreviated Stokes) and flow at high Reynolds numbers (High Re) on the side of the particle)(theta=90°. The y-axis is r/R, where r represents the distance from the particle along the flow direction and R is the particle radius, (−10=10 radiuses in front of the particle, 0=the surface of the particle, and +10=10 radiuses behind the particle). The x-axis is u/V, where u is the flow velocity on the particle surface and V is the approaching flow velocity.

Considering FIG. 4, for High Re, a maximum velocity ratio u/V is 2 on the surface. However, for Stokes flow, the velocity ratio is zero on the surface. This indicates that when two particles come close to each other with a fluid flow at low Reynolds numbers, the flow between the two particles is close to zero. In Stokes flow, there is no velocity increase at the maximum size of the particle, but velocity variations can occur even at 4 radiuses or more.

Figure 5:
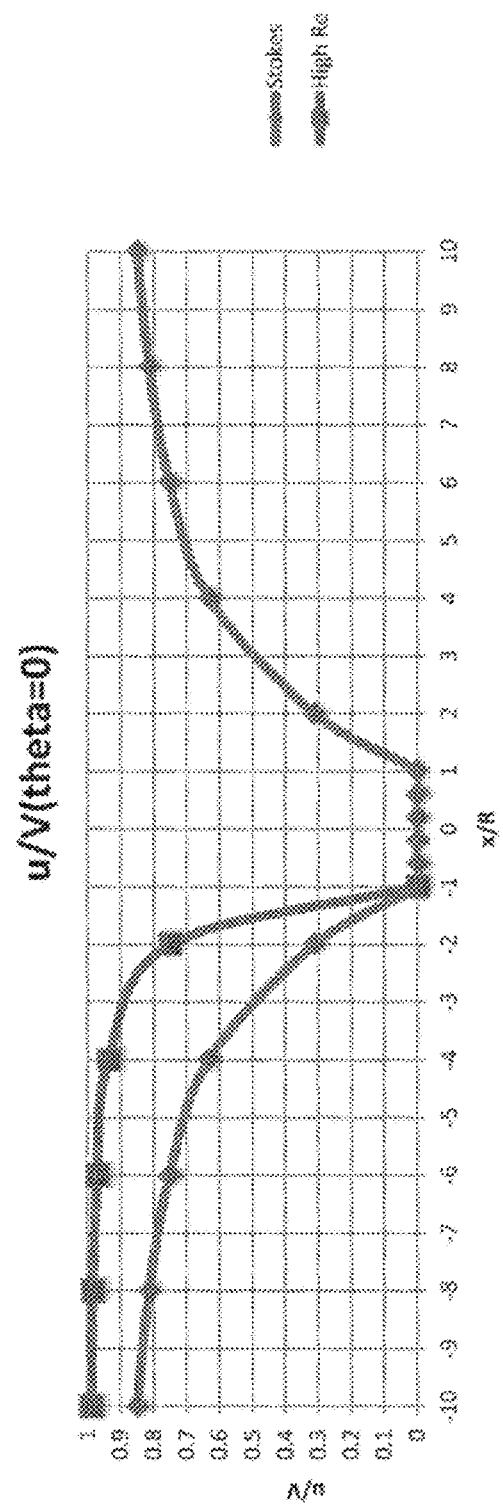
FIG. 5 is a graph illustrating the normalized flow velocity profile (u/V) over a sphere at the 0° location from the flow axis in terms of radiuses from the particle (x/R). The y-axis is u/V, and runs from 0 to 1 in intervals of 0.1. The x-axis is r/R, and runs from −10 to +10 in intervals of 1.

FIG. 5 is a graph illustrating the difference between Stokes flow (i.e. low Reynolds number, abbreviated Stokes) and flow at high Reynolds numbers (High Re) on the front of the particle)(theta=0°. For Stokes flow, the flowfield starts changing far in front of the particle, at values of x/R=6, whereas the High Re flow does not start changing until x/R=2.

An approximate analytical model can be developed to compare the fluid drag on an agglomerated cluster of particles versus the fluid drag on the individual particles. Four assumptions are made. First, interior particles on the cluster are shielded from shear forces. Second, there is no fluid flow between particles of the cluster; this is supported by FIG. 4. Third, the cluster of particles can be approximated as a sphere. Fourth, drag on the spherical cluster is Stokes drag.

The analytical model can be developed as follows:

$$\frac{F_D}{F_d} = \frac{\gamma}{\phi}\left(\frac{d}{D}\right)^2$$

where $F_D = 6\pi\mu DV$ is the total force on a spherical cluster of diameter D and $Fd = N6\pi\mu dV$ is the sum of all particle forces within the spherical cluster, assuming each particle has diameter d, using Stokes drag if flow passes through the clump at free stream velocity. In these equations, $\mu$ represents fluid viscosity, N represents the number of particles in the cluster, and $F_D/F_d$ is the ratio of the drag on the cluster to the drag on all of the individual particles that form the cluster. $\gamma$ (gamma) is the particle density divided by the fluid density. $\phi$ represents the concentration of particles in the cluster, or the percentage of the volume of the cluster that is occupied by particles. For equal spheres, the densest possible packing is about 74%.

Figure 6:
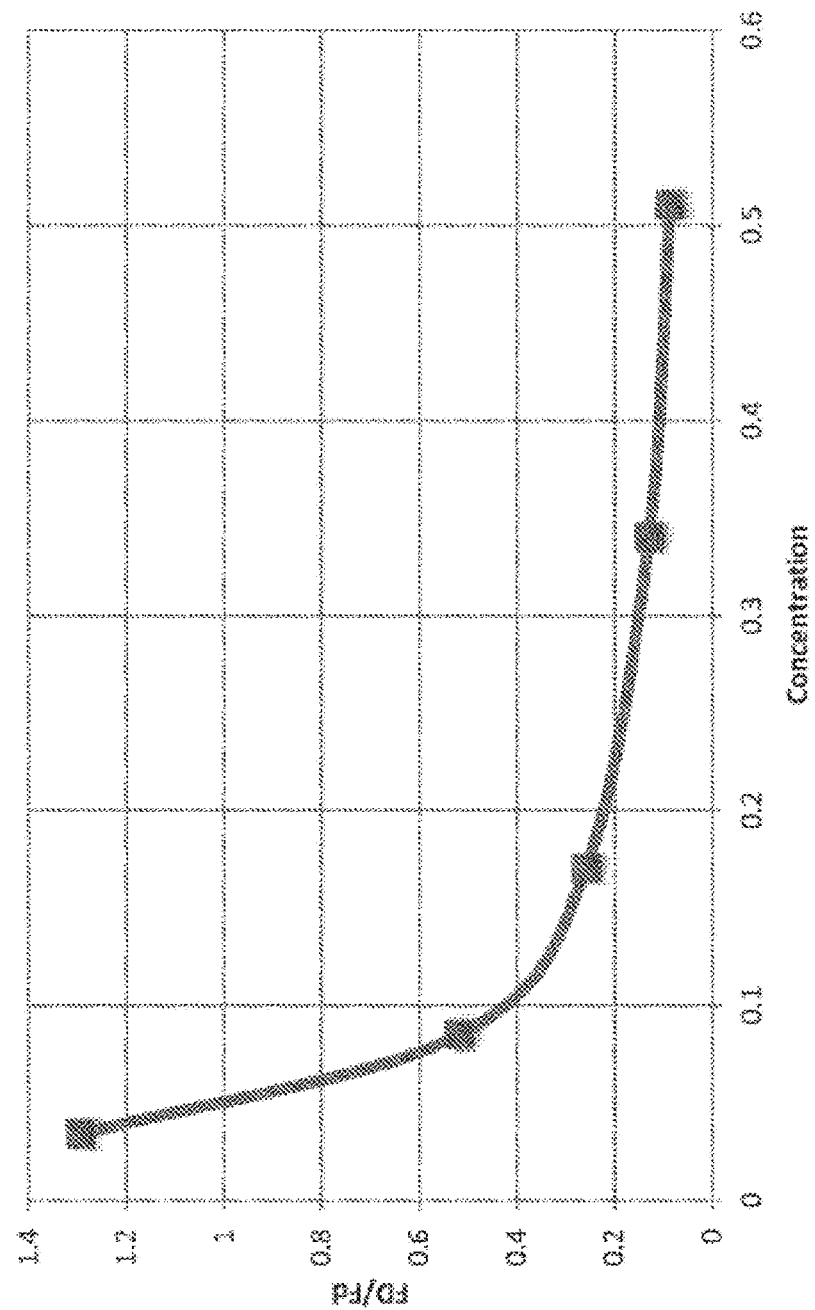
FIG. 6 is a graph of the ratio of the drag on a particle cluster over the total drag on the individual particles in the cluster (FD/Fd) versus the cluster concentration (i.e., the percent of the cluster volume occupied by particles). The y-axis runs from 0 to 1.4 in intervals of 0.2. The x-axis runs from 0 to 0.6 in intervals of 0.1.

FIG. 6 is a graph showing the $F_D/F_d$ versus concentration ($\phi$) when d/D=0.2, $\gamma$=1.1, and the Reynolds number is far less than 1. As seen here, the $F_D/F_d$ ratio is much smaller at higher concentrations. In other words, the reduction in drag increases as the density of the cluster increases.

Next, the effect of the Reynolds number and the particle concentration was tested using computation fluid dynamics (CFD). The cluster was simulated as a cubic cluster of 27 particles (3×3×3) with a spacing of 0.001 meters between particles. The Reynolds numbers tested were 0.01, 0.1, 1, 10, and 100, at a concentration of 11.3%. Particle concentrations were tested at 30%, 19%, 11.3%, 10%, 8%, 6%, 5%, 4%, 3%, 2%, and 1%, at Re=0.01. The particle concentration was varied by changing the spacing between the particles.

Figure 7:
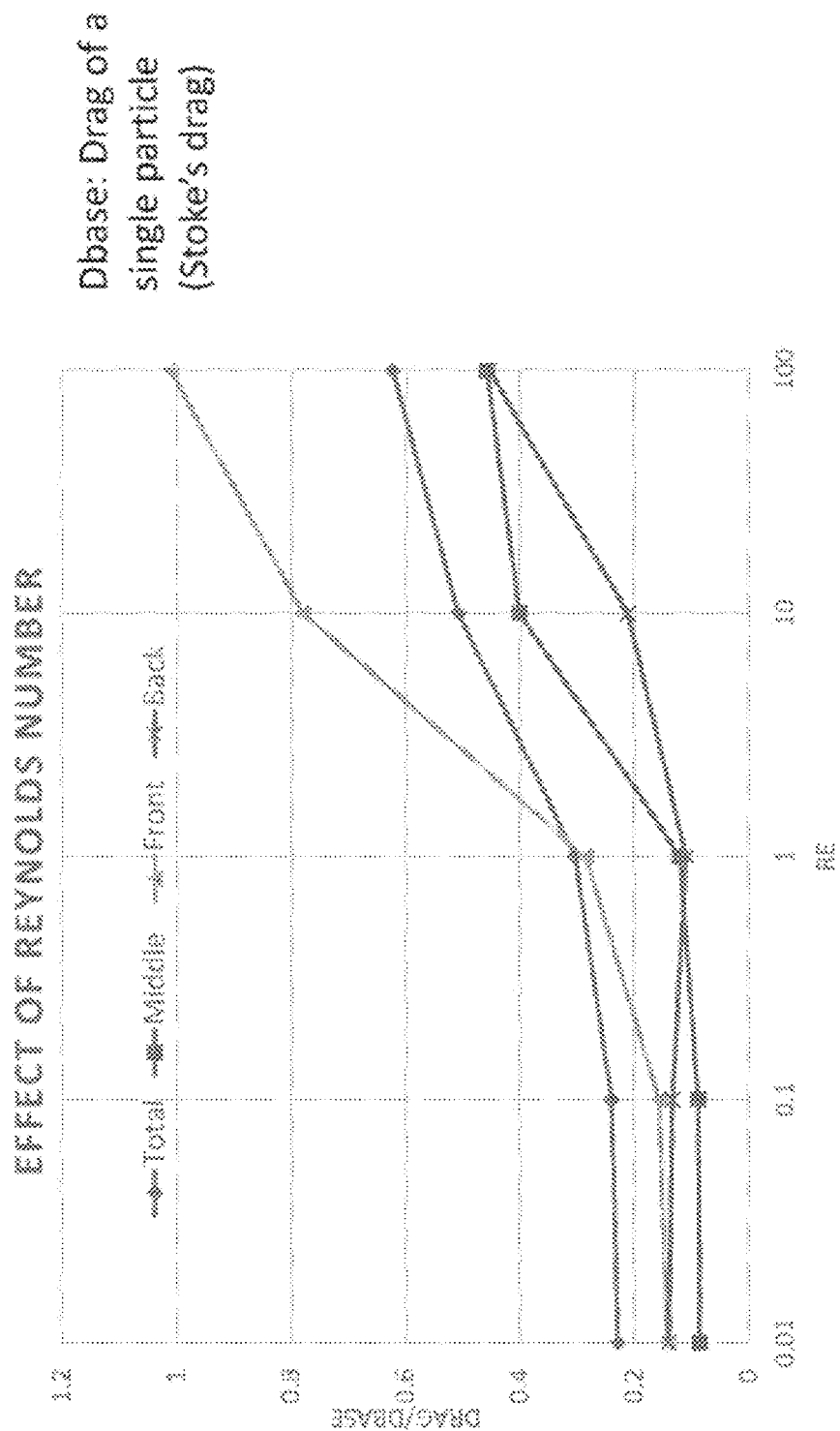
FIG. 7 is a graph showing the Drag/Dbase versus the Reynolds number for a simulation of 27 particles arranged in a 3×3×3 cubical array, with lines representing the ratios for the total drag and the drag on the front, middle, and back sets of particles. The y-axis runs from 0 to 1.2 in intervals of 0.2. The x-axis is logarithmic and is labeled 0.01, 0.1, 1, 10, and 100.

FIG. 7 is a graph showing the drag/Dbase versus the Reynolds number (Re) for four values: total, middle, front, and back. Front, Middle, and Back are the drag for the nine particles in the front, middle, and back locations of the cubic cluster. For these three lines, "Dbase" is the Stokes drag for nine isolated particles. "Total" is the total drag for the entire cluster of 27 particles, and for this value "Dbase" is the Stokes drag for 27 isolated particles. Generally, these results showed that a cluster of particles had less drag than isolated particles, regardless of their position in the cluster, at Re up to 100.

Figure 8:
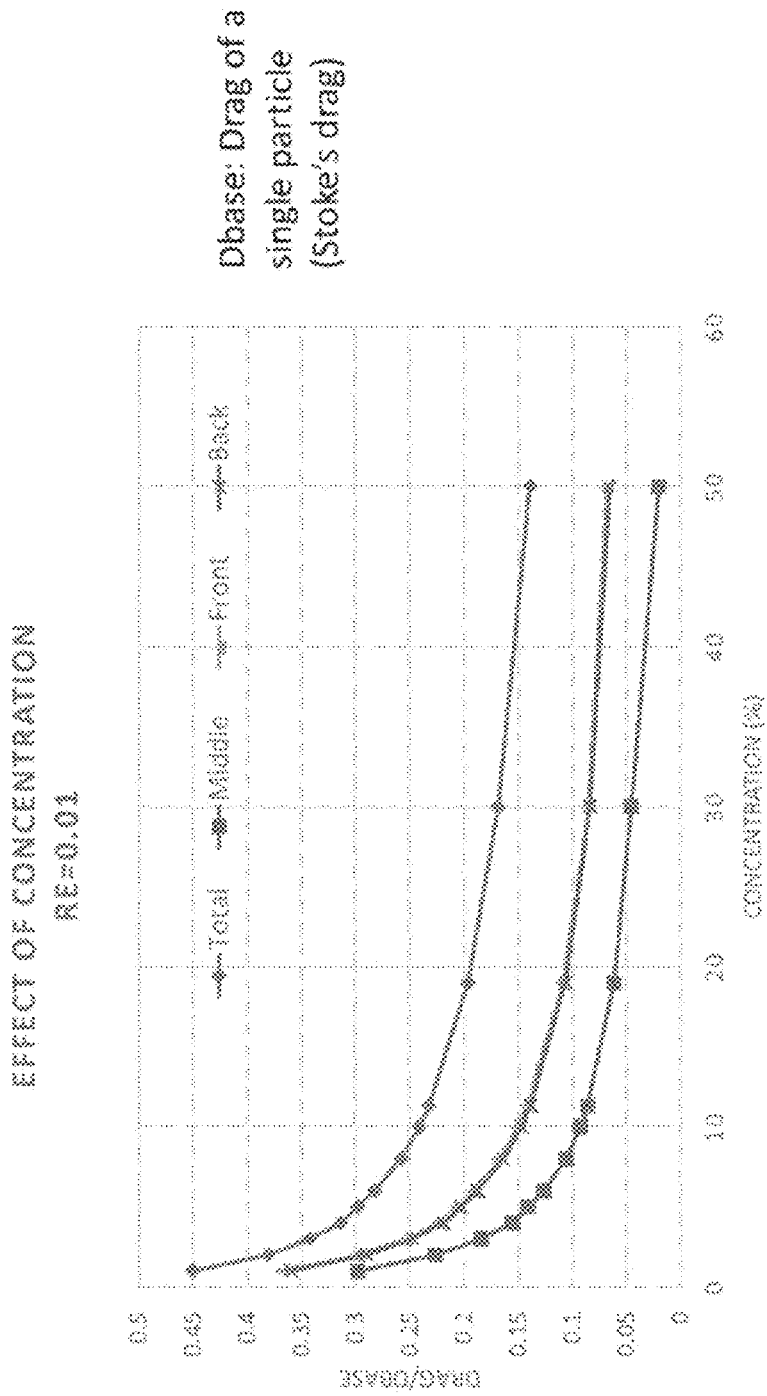
FIG. 8 is a graph showing the Drag/Dbase versus the particle concentration (%) for a simulation of 27 particles arranged in a 3×3×3 cubical array, with lines representing the ratios for the total drag and the drag on the front, middle, and back sets of particles. The y-axis runs from 0 to 0.5 in intervals of 0.05. The x-axis runs from 0 to 60 in intervals of 10.

FIG. 8 is a graph showing drag/Dbase versus the concentration. The lines have the same meaning as in FIG. 7. This graph confirms the reduction in drag as the concentration increases.

It is noted that the drag reduction effect seen in FIG. 7 and FIG. 8 is a localized effect, and happens only when the particles in the cluster are very close together (localized, i.e. the particle concentration is very high) with clear fluid flowing around the cluster. In FIG. 7 and FIG. 8, the spacing between particles was 0.001. When the model was rerun with spacing between particles close to 0.1 and Re=0.01 such that the particles were spaced far apart and were not localized, the total drag on the "Middle" particles alone was equal to the total drag of the isolated particles at n=75. This indicates that drag increases if the particles in the cluster are not tightly packed, even at lower Re, which is consistent with literature.

The analytical model shows that with Stokes flow, fluid drag decreases dramatically once clumping begins. This results from the decrease in velocity between particles caused by shear forces dominant shear forces in the flow-field. It is thus desirable to have the particles cluster as quickly as possible to get good trapping. The lateral acoustic radiation forces generated by the multi-dimensional acoustic standing wave are then capable of overcoming fluid drag force and driving the particles to clustering regions, packing them more tightly until they gravity separate. More importantly, higher flowrates may be possible with the use of lower frequencies. Longer wavelengths at these lower frequencies would result in a larger D/d ratio, which means the same acoustic force would be capable of trapping the particle clusters with higher velocity flow. The analytical model further suggests that better trapping can be achieved with higher local concentration, which leads to tightly packed cylindrical clusters.

Prior to discussing further optimization of the systems, it is helpful to provide an explanation now of how multi-dimensional acoustic standing waves are generated. The multi-dimensional acoustic standing wave needed for particle collection is obtained by driving an ultrasonic transducer at a frequency that both generates the acoustic standing wave and excites a fundamental 3D vibration mode of the transducer crystal. Perturbation of the piezoelectric crystal in an ultrasonic transducer in a multimode fashion allows for generation of a multidimensional acoustic standing wave. A piezoelectric crystal can be specifically designed to deform in a multimode fashion at designed frequencies, allowing for generation of a multi-dimensional acoustic standing wave. The multi-dimensional acoustic standing wave may be generated by distinct modes of the piezoelectric crystal such as a 3×3 mode that would generate multidimensional acoustic standing waves. A multitude of multidimensional acoustic standing waves may also be generated by allowing the piezoelectric crystal to vibrate through many different mode shapes. Thus, the crystal would excite multiple modes such as a 0×0 mode (i.e. a piston mode) to a 1×1, 2×2, 1×3, 3×1, 3×3, and other higher order modes and then cycle back through the lower modes of the crystal (not necessarily in straight order). This switching or dithering of the crystal between modes allows for various multidimensional wave shapes, along with a single piston mode shape to be generated over a designated time.

Some further explanation of the ultrasonic transducers used in the devices, systems, and methods of the present disclosure may be helpful as well. In this regard, the transducers use a piezoelectric crystal, usually made of PZT-8 (lead zirconate titanate). Such crystals may have a 1 inch diameter and a nominal 2 MHz resonance frequency, and may also be of a larger size. Each ultrasonic transducer module can have only one crystal, or can have multiple crystals that each act as a separate ultrasonic transducer and are either controlled by one or multiple amplifiers. The crystals can be square, rectangular, irregular polygon, or generally of any arbitrary shape. The transducer(s) is/are used to create a pressure field that generates forces of the same order of magnitude both orthogonal to the standing wave direction (lateral) and in the standing wave direction (axial).

Figure 9:
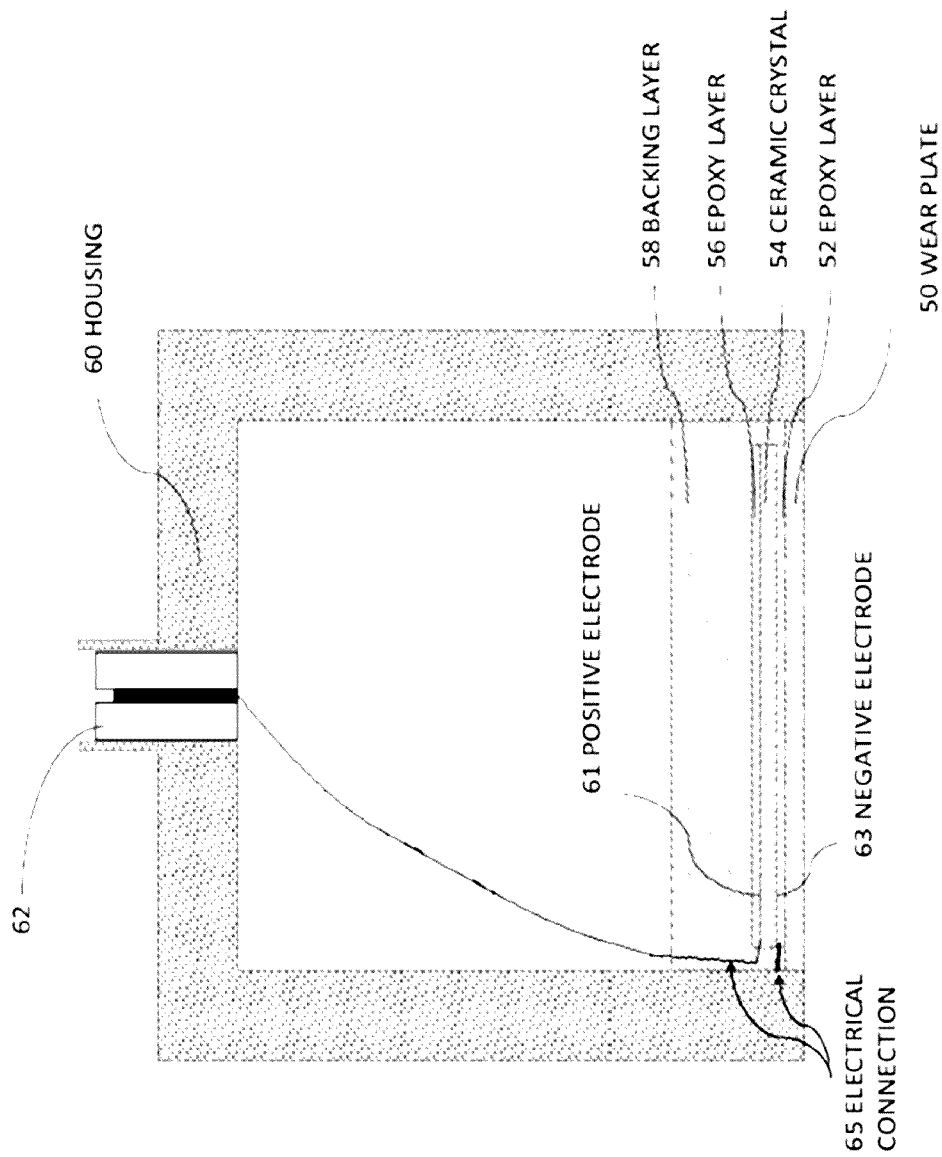
FIG. 9 is a cross-sectional diagram of a conventional ultrasonic transducer.

FIG. 9 is a cross-sectional diagram of a conventional ultrasonic transducer. This transducer has a wear plate 50 at a bottom end, epoxy layer 52, ceramic crystal 54 (made of, e.g. PZT), an epoxy layer 56, and a backing layer 58. On either side of the ceramic crystal, there is an electrode: a positive electrode 61 and a negative electrode 63. The epoxy layer 56 attaches backing layer 58 to the crystal 54. The entire assembly is contained in a housing 60 which may be made out of, for example, aluminum. An electrical adapter 62 provides connection for wires to pass through the housing and connect to leads (not shown) which attach to the crystal 54. Typically, backing layers are designed to add damping and to create a broadband transducer with uniform displacement across a wide range of frequency and are designed to suppress excitation at particular vibrational eigen-modes. Wear plates are usually designed as impedance transformers to better match the characteristic impedance of the medium into which the transducer radiates.

Figure 10:
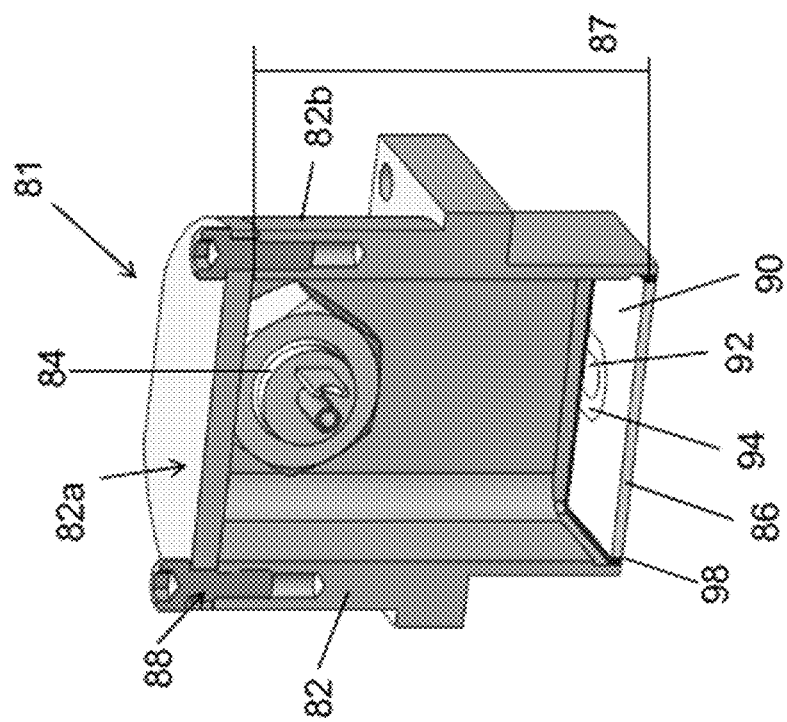
FIG. 10 is a cross-sectional diagram of an ultrasonic transducer of the present disclosure. An air gap is present within the transducer, and no backing layer or wear plate is present.

FIG. 10 is a cross-sectional view of an ultrasonic transducer 81 of the present disclosure. Transducer 81 is shaped as a disc or a plate, and has an aluminum housing 82. The piezoelectric crystal is a mass of perovskite ceramic crystals, each consisting of a small, tetravalent metal ion, usually titanium or zirconium, in a lattice of larger, divalent metal ions, usually lead or barium, and O2-ions. As an example, a PZT (lead zirconate titanate) crystal 86 defines the bottom end of the transducer, and is exposed from the exterior of the housing. The crystal is supported on its perimeter by a small elastic layer 98, e.g. silicone or similar material, located between the crystal and the housing. Put another way, no wear layer is present. In particular embodiments, the crystal is an irregular polygon, and in further embodiments is an asymmetrical irregular polygon.

Figure 11:
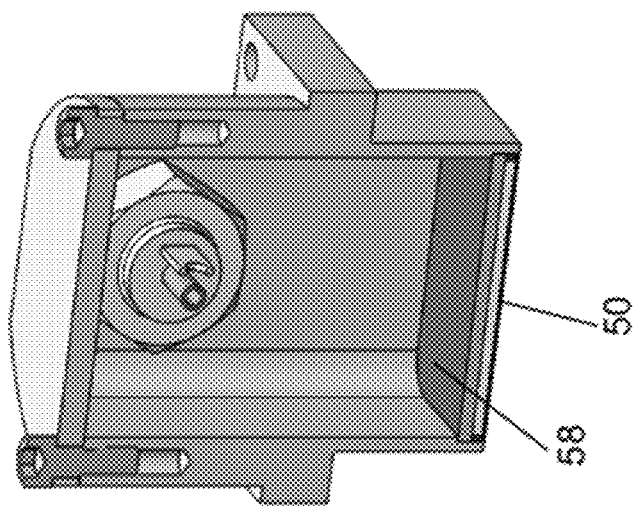
FIG. 11 is a cross-sectional diagram of an ultrasonic transducer of the present disclosure. An air gap is present within the transducer, and a backing layer and wear plate are present.

Screws 88 attach an aluminum top plate 82*a* of the housing to the body 82*b* of the housing via threads. The top plate includes a connector 84 for powering the transducer. The top surface of the PZT crystal 86 is connected to a positive electrode 90 and a negative electrode 92, which are separated by an insulating material 94. The electrodes can be made from any conductive material, such as silver or nickel. Electrical power is provided to the PZT crystal 86 through the electrodes on the crystal. Note that the crystal 86 has no backing layer or epoxy layer. Put another way, there is an air gap 87 in the transducer between aluminum top plate 82*a* and the crystal 86 (i.e. the air gap is completely empty). A minimal backing 58 and/or wear plate 50 may be provided in some embodiments, as seen in FIG. 11.

The transducer design can affect performance of the system. A typical transducer is a layered structure with the ceramic crystal bonded to a backing layer and a wear plate. Because the transducer is loaded with the high mechanical impedance presented by the standing wave, the traditional design guidelines for wear plates, e.g., half wavelength thickness for standing wave applications or quarter wavelength thickness for radiation applications, and manufacturing methods may not be appropriate. Rather, in one embodiment of the present disclosure the transducers, there is no wear plate or backing, allowing the crystal to vibrate in one of its eigenmodes (i.e. near eigenfrequency) with a high Q-factor. The vibrating ceramic crystal/disk is directly exposed to the fluid flowing through the flow chamber.

Removing the backing (e.g. making the crystal air backed) also permits the ceramic crystal to vibrate at higher order modes of vibration with little damping (e.g. higher order modal displacement). In a transducer having a crystal with a backing, the crystal vibrates with a more uniform displacement, like a piston. Removing the backing allows the crystal to vibrate in a non-uniform displacement mode. The higher order the mode shape of the crystal, the more nodal lines the crystal has. The higher order modal displacement of the crystal creates more trapping lines, although the correlation of trapping line to node is not necessarily one to one, and driving the crystal at a higher frequency will not necessarily produce more trapping lines.

In some embodiments, the crystal may have a backing that minimally affects the Q-factor of the crystal (e.g. less than 5%). The backing may be made of a substantially acoustically transparent material such as balsa wood, foam, or cork which allows the crystal to vibrate in a higher order mode shape and maintains a high Q-factor while still providing some mechanical support for the crystal. The backing layer may be a solid, or may be a lattice having holes through the layer, such that the lattice follows the nodes of the vibrating crystal in a particular higher order vibration mode, providing support at node locations while allowing the rest of the crystal to vibrate freely. The goal of the lattice work or acoustically transparent material is to provide support without lowering the Q-factor of the crystal or interfering with the excitation of a particular mode shape.

Placing the crystal in direct contact with the fluid also contributes to the high Q-factor by avoiding the dampening and energy absorption effects of the epoxy layer and the wear plate. Other embodiments may have wear plates or a wear surface to prevent the PZT, which contains lead, contacting the host fluid. This may be desirable in, for example, biological applications such as separating blood. Such applications might use a wear layer such as chrome, electrolytic nickel, or electroless nickel. Chemical vapor deposition could also be used to apply a layer of poly(p-xylylene) (e.g. Parylene) or other polymers or polymer films. Organic and biocompatible coatings such as silicone or polyurethane are also usable as a wear surface.

Figure 12:
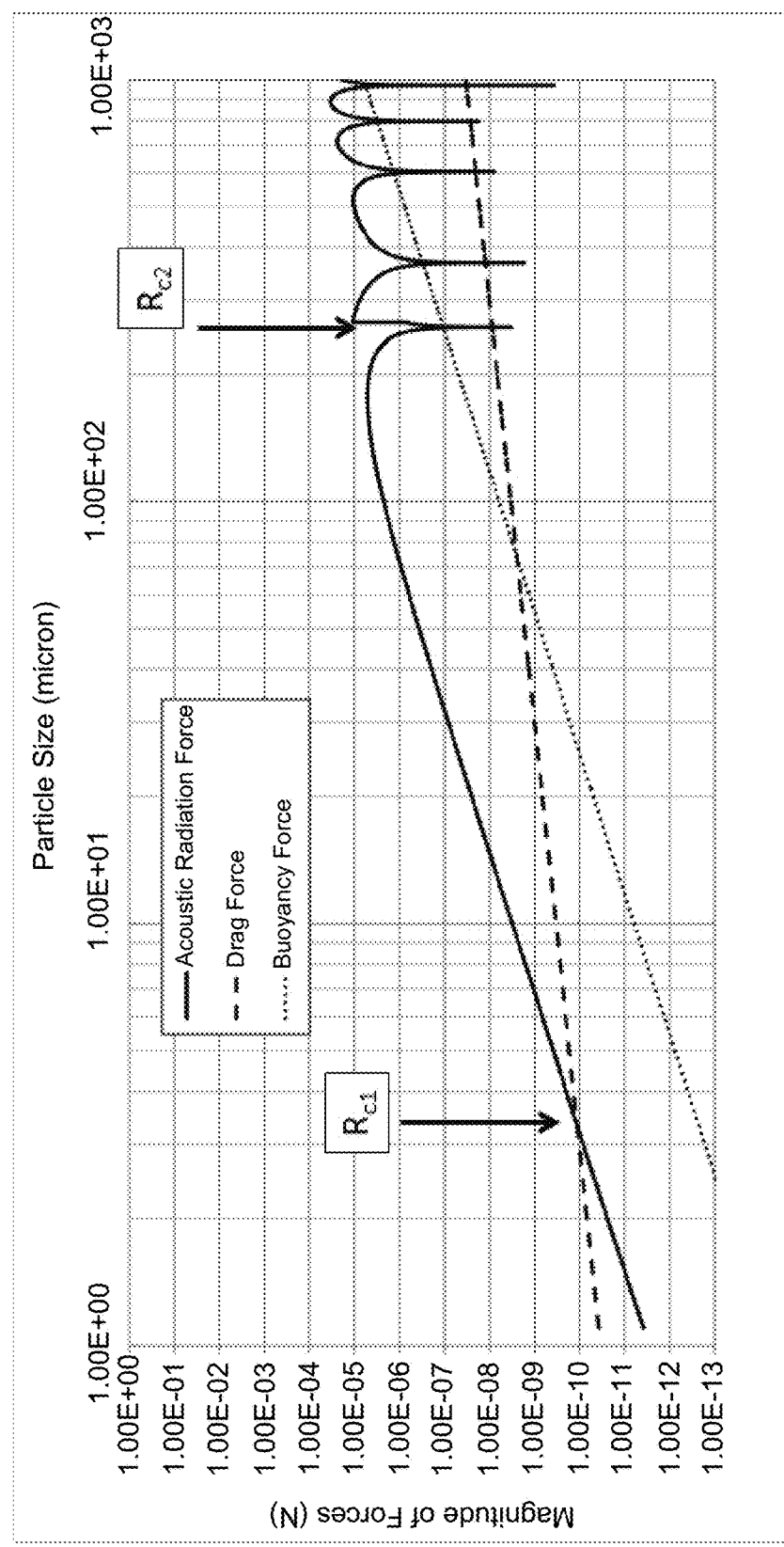
FIG. 12 is a graph showing the relationship of the acoustic radiation force, buoyancy force, and Stokes' drag force to particle size. The horizontal axis is in microns (μm) and the vertical axis is in Newtons (N).

FIG. 12 is a log-log graph (logarithmic y-axis, logarithmic x-axis) that shows the scaling of the acoustic radiation force, fluid drag force, and buoyancy force with particle radius, and provides an explanation for the separation of particles using acoustic radiation forces. The buoyancy force is a particle volume dependent force, and is therefore negligible for particle sizes on the order of micron, but grows, and becomes significant for particle sizes on the order of hundreds of microns. The fluid drag force (Stokes drag force) scales linearly with fluid velocity, and therefore typically exceeds the buoyancy force for micron sized particles, but is negligible for larger sized particles on the order of hundreds of microns. The acoustic radiation force scaling is different. When the particle size is small, Gor'kov's equation is accurate and the acoustic trapping force scales with the volume of the particle. Eventually, when the particle size grows, the acoustic radiation force no longer increases with the cube of the particle radius, and will rapidly vanish at a certain critical particle size. For further increases of particle size, the radiation force increases again in magnitude but with opposite phase (not shown in the graph). This pattern repeats for increasing particle sizes.

Initially, when a suspension is flowing through the system with primarily small micron sized particles, it is necessary for the acoustic radiation force to balance the combined effect of fluid drag force and buoyancy force for a particle to be trapped in the standing wave. In FIG. 12 this happens at a particle size labeled as $R_{c1}$. The graph then indicates that all larger particles will be trapped as well. Therefore, when small particles are trapped in the standing wave, particles coalescence/clumping/aggregation/agglomeration takes place, resulting in continuous growth of effective particle size. As particles cluster, the total drag on the cluster is much lower than the sum of the drag forces on the individual particles. In essence, as the particles cluster, they shield each other from the fluid flow and reduce the overall drag of the cluster. As the particle cluster size grows, the acoustic radiation force reflects off the cluster, such that the net acoustic radiation force decreases per unit volume. The acoustic lateral forces on the particles must be larger than the drag forces for the clusters to remain stationary and grow in size.

Particle size growth continues until the buoyancy force becomes dominant, which is indicated by a second critical particle size, $R_{c2}$. The buoyancy force per unit volume of the cluster remains constant with cluster size, since it is a function of the particle density, cluster concentration and gravity constant. Therefore, as the cluster size increases, the buoyancy force on the cluster increases faster than the acoustic radiation force. At the size $R_{c2}$, the particles will rise or sink, depending on their relative density with respect to the host fluid. At this size, acoustic forces are secondary, gravity/buoyancy forces become dominant, and the particles naturally drop out or rise out of the host fluid. Not all particles will drop out, and those remaining particles and new particles entering the acoustic chamber will continue to move to the three-dimensional nodal locations, repeating the growth and drop-out process. This phenomenon explains the quick drops and rises in the acoustic radiation force beyond size $R_{c2}$. Thus, FIG. 12 explains how small particles can be trapped continuously in a standing wave, grow into larger particles or clumps, and then eventually will rise or settle out because of increased buoyancy force.

The size, shape, and thickness of the transducer determine the transducer displacement at different frequencies of excitation, which in turn affects particle separation efficiency. Higher order modal displacements generate three-dimensional acoustic standing waves with strong gradients in the acoustic field in all directions, thereby creating equally strong acoustic radiation forces in all directions, leading to multiple trapping lines, where the number of trapping lines correlate with the particular mode shape of the transducer.

Figure 13:
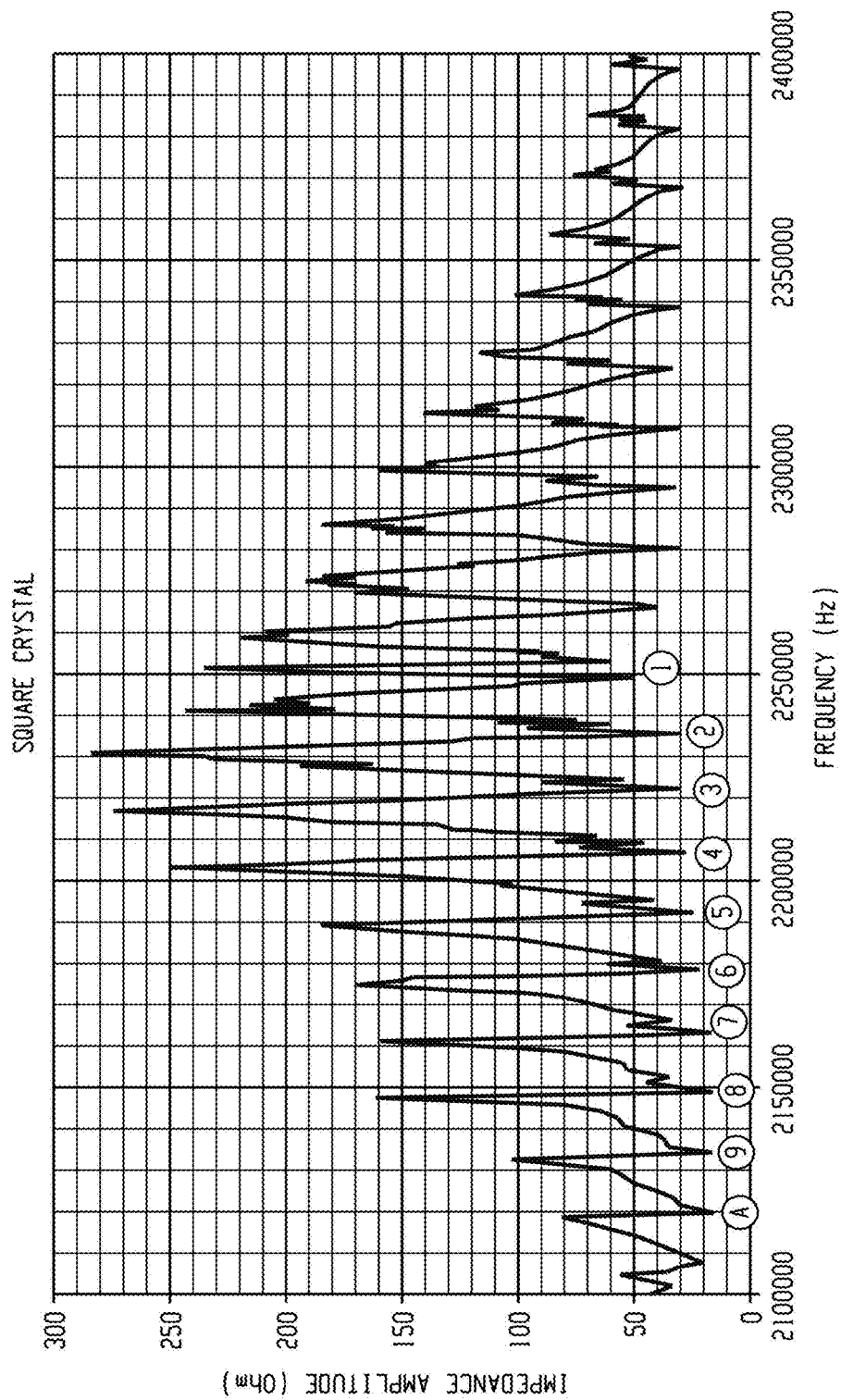
FIG. 13 is a graph of electrical impedance amplitude versus frequency for a square transducer driven at different frequencies.

FIG. 13 shows the measured electrical impedance amplitude of the transducer as a function of frequency in the vicinity of the 2.2 MHz transducer resonance. The minima in the transducer electrical impedance correspond to acoustic resonances of a water column and represent potential frequencies for operation. Numerical modeling has indicated that the transducer displacement profile varies significantly at these acoustic resonance frequencies, and thereby directly affects the acoustic standing wave and resulting trapping force. Since the transducer operates near its thickness resonance, the displacements of the electrode surfaces are essentially out of phase. The typical displacement of the transducer electrodes is not uniform and varies depending on frequency of excitation. Higher order transducer displacement patterns result in higher trapping forces and multiple stable trapping lines for the captured particles.

To investigate the effect of the transducer displacement profile on acoustic trapping force and particle separation efficiencies, an experiment was repeated ten times, with all conditions identical except for the excitation frequency. Ten consecutive acoustic resonance frequencies, indicated by circled numbers 1-9 and letter A on FIG. 13, were used as excitation frequencies. The conditions were experiment duration of 30 min, a 1000 ppm oil concentration of approximately 5-micron SAE-30 oil droplets, a flow rate of 500 ml/min, and an applied power of 20 W.

As the emulsion passed by the transducer, the trapping lines of oil droplets were observed and characterized. The characterization involved the observation and pattern of the number of trapping lines across the fluid channel, as shown in FIG. 14A, for seven of the ten resonance frequencies identified in FIG. 13.

FIG. 14B shows an isometric view of the system in which the trapping line locations are being determined. FIG. 14C is a view of the system as it appears when looking down the inlet, along arrow 114. FIG. 14D is a view of the system as it appears when looking directly at the transducer face, along arrow 116.

The effect of excitation frequency clearly determines the number of trapping lines, which vary from a single trapping line at the excitation frequency of acoustic resonance 5 and 9, to nine trapping lines for acoustic resonance frequency 4. At other excitation frequencies four or five trapping lines are observed. Different displacement profiles of the transducer can produce different (more) trapping lines in the standing waves, with more gradients in displacement profile generally creating higher trapping forces and more trapping lines. It is noted that although the different trapping line profiles shown in FIG. 14A were obtained at the frequencies shown in FIG. 13, these trapping line profiles can also be obtained at different frequencies.

FIG. 14A shows the different crystal vibration modes possible by driving the crystal to vibrate at different fundamental frequencies of vibration. The 3D mode of vibration of the crystal is carried by the acoustic standing wave across the fluid in the chamber all the way to the reflector and back. The resulting multi-dimensional standing wave can be thought of as containing two components. The first component is a planar out-of-plane motion component (uniform displacement across crystal surface) of the crystal that generates a standing wave, and the second component is a displacement amplitude variation with peaks and valleys occurring in both lateral directions of the crystal surface. Three-dimensional force gradients are generated by the standing wave. These three-dimensional force gradients result in lateral radiation forces that stop and trap the particles with respect to the flow by overcoming the viscous drag force. In addition, the lateral radiation forces are responsible for creating tightly packed clusters of particles. Therefore, particle separation and gravity-driven collection depends on generating a multi-dimensional standing wave that can overcome the particle drag force as the mixture flows through the acoustic standing wave. Multiple particle clusters are formed along trapping lines in the axial direction of the standing wave, as presented schematically in FIG. 14A.

Figure 15B:
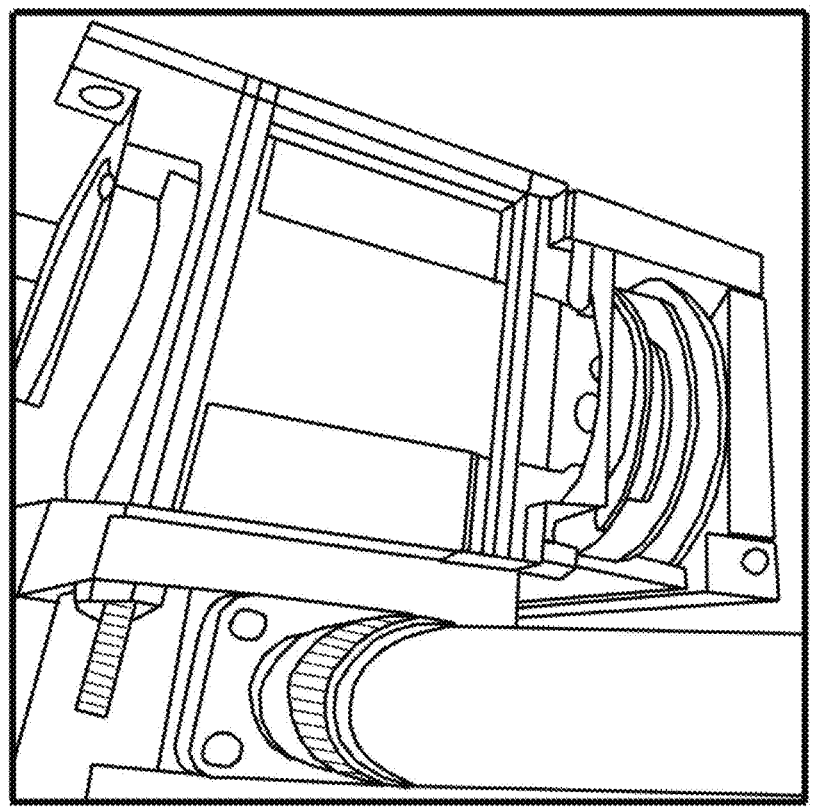
FIG. 15B is a side view.
Figure 15A:
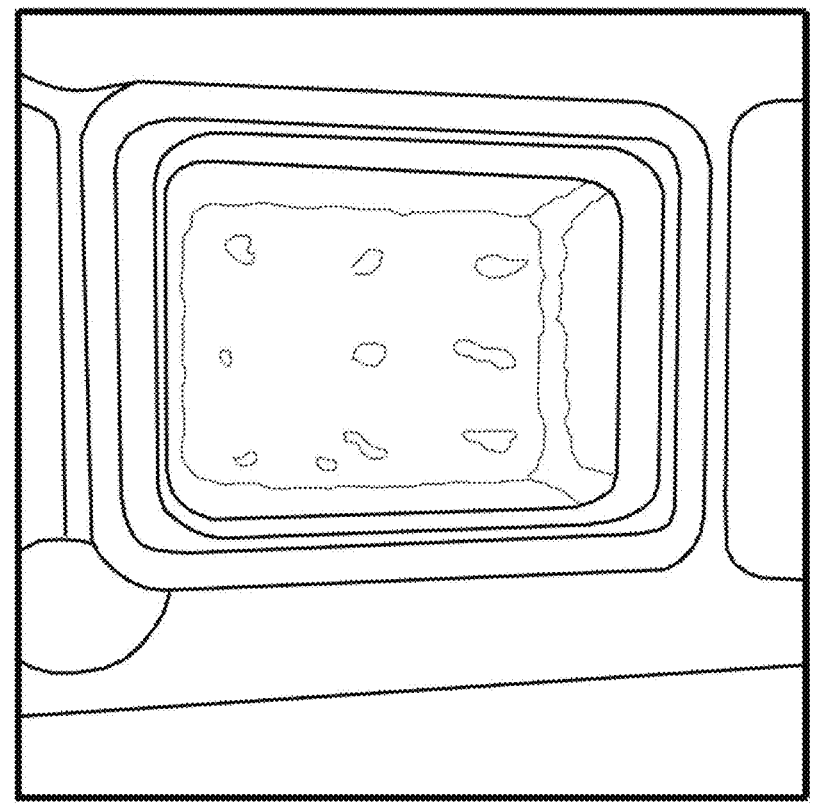
FIG. 15A is a front view photograph of a working 1 inch by 1 inch separator system using a 1 inch by 1 inch crystal driven to a (3,3) mode with a yeast mixture.

FIG. 15A is a photograph of a working 1 inch by 1 inch separator system using a 1 inch by 1 inch crystal driven to a 3×3 mode with a yeast mixture at a frequency of 2 MHz and a flow rate of 30 mL/min. This is a front view of the system, and shows nine trapping lines created by the lateral radiation forces of the multi-dimensional acoustic standing wave. FIG. 15B is a side view of the system, and shows that the trapping lines span the entire width of the acoustic chamber (i.e., between the transducer to the reflector). The system was operated continuously at near 90% clarification for a 1.5% yeast mixture with a packed cell mass of >50% in the concentrated cell stream.

Figure 16:
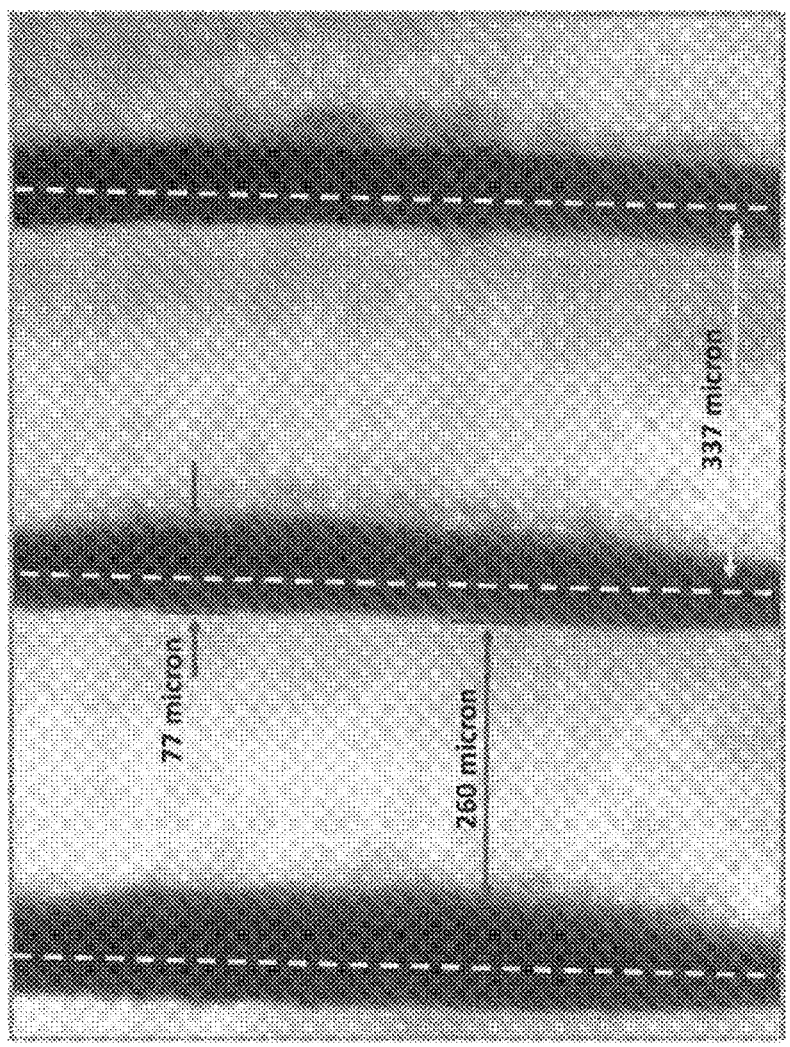
FIG. 16 is a screenshot of a video of a trapping line, showing yeast particle clusters parallel to the direction of flow (direction of flow is upward in screenshot), and clear channels of fluid between the clusters.

In FIG. 16, a 1 inch by 1 inch acoustic chamber was used with a fluid feed rate of 15 ml/minute (peristaltic). The ultrasonic transducer(s) was operated at a frequency of 2.23 MHz and ~7 W power, and the fluid was a 3% yeast solution. FIG. 16 is a 200× magnification of the trapping that occurred, showing three trapping lines separated by 260 and 337 microns, respectively, with a width of approximately 77 microns. If the speed of sound is 1,484 m/s, the expected half wavelength at the operated frequency is 333 microns. As seen here, as the particles form clusters, channels of fluid are formed between the clusters, thereby allowing for improved aggregation and separation of the particles. It is noted that when the clusters finally separate and fall, the clear fluid in the channels between clusters also falls. This occurs because there is less viscous resistance for the fluid to go around the clusters than through these narrow channels between the clusters as they fall.

The system depicted in FIG. 1 is similar to that of FIG. 16, and uses a 3 inch×3 inch×3 inch acoustic chamber with four 1.5 inch by 1.5 inch 2 MHz PZT-8 transducers. The system of FIG. 1 was operated continuously at near 90% clarification for a 1.5% yeast mixture with flowrates of about 270 ml/min, and a packed cell mass of >50% in the concentrated cell stream. The same system has been operated effectively for the clarification of protein from a CHO/protein cell mixture. Such applications are important in the advancement of the biopharmaceutical industry.

At low Reynolds numbers, the drag is a result of shear forces only, or the flow is fully viscous. Viscous flow prefers to move in planes, or laminar layers. Any three dimensionality tends to increase drag. Thus, at low Reynolds numbers, the following equations present drag coefficients ($C_D$) as a function of particle Reynolds numbers (Re):

$$\text{Sphere: } C_D = \frac{24}{Re}(1 + 0.15\ Re^{0.678})$$

for $$0 < Re \leq 2 \times 10^5$$

$$\text{Cylinder: } C_D \approx 1 + 10 Re^{-2/3}$$

for $$1 < Re \leq 2 \times 10^5$$

The equations show that the drag coefficient of a cylinder is lower than a sphere at Reynolds numbers less than ten. Furthermore, a cylinder can carry significantly more particles for a given projected area. This means a cylindrical particle cluster will have higher gravity forces and lower resistance drag than a spherical particle cluster at low Reynolds numbers. Therefore, a cylindrical particle cluster will drop out or rise out of the fluid faster than other shapes. As a result, it is important to choose an electrical signal drive frequency for the acoustophoretic separation system that gives the best cylindrical cluster generation for drop out or rise out.

Figure 17:
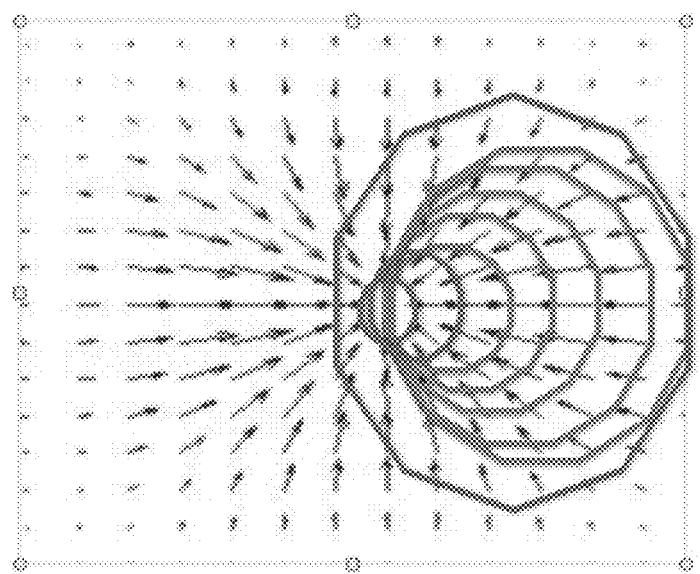
FIG. 17 is a schematic of the lateral forces near one trapping line, with several different particle cluster diameters shown.

FIG. 17 shows the effect of the lateral force variation on particle clustering. This figure shows the predicted lateral forces (based on a COMSOL simulation) near one node or trapping line, along with several different particle cluster diameters. The arrow lengths represent the lateral radiation force magnitude. At the center of the node, there is no force, and the other lateral forces will drive all the particles towards this location. This would be the cluster location if there were no other forces. Three different forces act on any cluster: $F_L$, $F_D$, and $F_G$. $F_L$ represents the sum of all the lateral acoustic radiation particle forces. $F_D$ is the fluid drag force of the cylindrical cluster. $F_G$ is the force of gravity pulling down on the cluster particles. The drag force $F_D$ on a particle cluster will be an order of magnitude smaller than the lateral radiation force $F_L$ or gravity force $F_G$ on the cylindrical clusters. Therefore, the gravity force will be offset by the lateral radiation force. The cluster has to move down slightly to have a net upwards lateral radiation force (lateral direction is the flow direction). In other words, if each force vector inside a cluster represents a force on a particle in the cluster, the net force on the cylindrical cluster is the sum of all the particle forces. The particle forces get larger as the cluster moves downwards. Therefore, the net radiation force (or the sum of all the up vectors) on the cluster increases as the cluster moves down.

The key thing to notice is that the upward forces on the enclosed particles vary from zero at the node to a maximum value at the anti-node. The total lateral radiation force per unit volume will therefore decrease with cluster size; it does not stay constant. This is consistent with the decrease in drag force per unit particle as the cluster size increases. As the cluster diameter increases, it has to include particles with radiation forces acting in the downward direction. This is extremely important.

The density of the particles and the volume of the cluster will determine the gravity force as long as the particle concentration of the cluster is constant. The gravity force per unit volume is therefore constant as a particle cluster increases in size. Therefore, the lateral radiation forces will move the particles in the planes towards the nodes. These clusters will locate below the nodes at an equilibrium position where the radiation forces can hold the cluster in suspension as it grows. As they grow in size, the net lateral force per unit volume will decrease while the net gravity force per unit size will be constant. The center of the cluster will continue to shift down with cluster size until it is at the maximum lateral force location. At some cluster size, the gravity force will dominate, and the cluster will fall out of suspension. When this happens, the cycle will repeat and new clusters will form, thereby permitting the system to continuously operate.

The drop out cluster diameter will be determined by the forces acting on the particles in the clusters. The lateral radiation force is a function of the lateral acoustic pressure field generated by the multi-dimensional acoustic standing wave. There are several formulations for radiation pressure experienced by a sphere inside an acoustic field. The most widely used formulation for acoustic radiation forces is by Gork'ov, where the primary acoustic radiation force $F_A$ is defined as a function of a field potential U, $F_A = -\nabla(U)$, where the field potential U is defined as $$U = V_0 \left[ \frac{\langle p^2(x, y, t) \rangle}{2\rho_f c_f^2} f_1 - \frac{3\rho_f \langle v^2(x, y, t) \rangle}{4} f_2 \right]$$

and $f_1$ and $f_2$ are the monopole and dipole contributions defined by $$f_1 = 1 - \frac{1}{\Lambda \sigma^2}$$

$$f_2 = \frac{2(\Lambda - 1)}{2\Lambda + 1},$$

where $$\sigma = \frac{c_p}{c_f}$$

$$\Lambda = \frac{\rho_p}{\rho_f}$$

$$\beta_f = \frac{1}{\rho_f c_f^2}$$

where p is the acoustic pressure, u is the fluid particle velocity, $\Lambda$ is the ratio of cell density $\rho_p$ to fluid density $\rho_f$, $\sigma$ is the ratio of cell sound speed $c_p$ to fluid sound speed $c_f$, $V_o$ is the volume of the cell, and < > indicates time averaging over the period of the wave.

Gork'ov's model is for a single particle in a standing wave and is limited to particle sizes that are small with respect to the wavelength of the sound fields in the fluid and the particle. It also does not take into account the effect of viscosity of the fluid and the particle on the radiation force. As a result, this model cannot be used for the macro-scale ultrasonic separators discussed herein since particle clusters can grow quite large. A more complex and complete model for acoustic radiation forces that is not limited by particle size was therefore used. The models that were implemented are based on the theoretical work of Yurii Ilinskii and Evgenia Zabolotskaya as described in AIP Conference Proceedings, Vol. 1474-1, pp. 255-258 (2012). These models also include the effect of fluid and particle viscosity, and therefore are a more accurate calculation of the acoustic radiation force.

Figure 18:
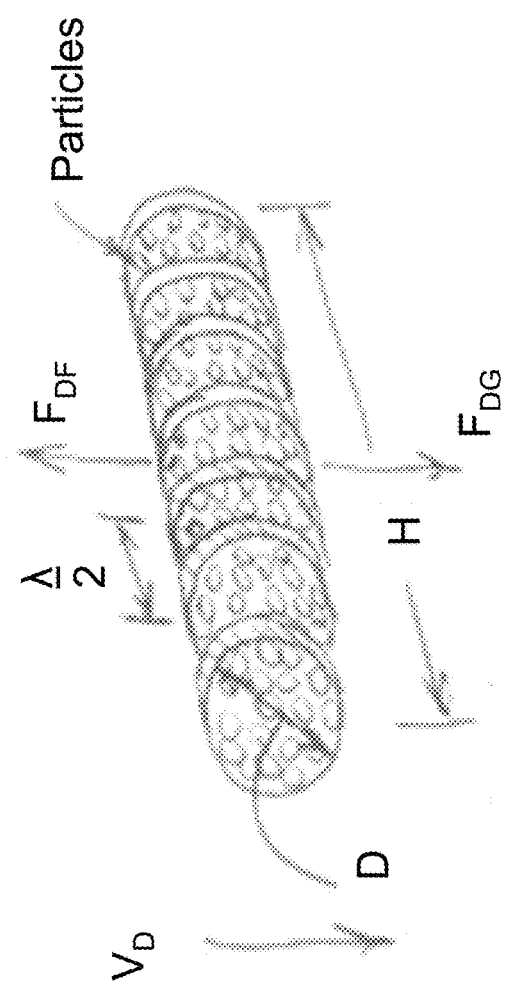
FIG. 18 is a diagram showing the cluster terminal velocity based upon the cluster drag and gravitational forces.

FIG. 18 is an illustration of a portion of a trapping line. As seen here, the particle clusters are in the shape of cylindrical disks, or "hockey pucks", with a diameter D and a distance of $\lambda/2$ between their centers. The trapping line has a height H, and there are three forces working on the trapping line. $F_{DF}$ is the fluid draft force (i.e. the flow of fluid is in the upwards direction). $F_{DG}$ is the gravity drag force downwards, and $V_D$ is the terminal velocity or cluster drop velocity.

The cluster terminal velocity is obtained by equating the cluster drag force ($F_{DF}$) and gravity drag force ($F_{DG}$). The resulting equations for a cylindrical cluster are presented in FIG. 19. In FIG. 19, $C_D$ is the drag coefficient of the cylinder; $\rho_p$ is the particle density; $\rho_f$ is the fluid density; g is the gravity of Earth, i.e. ~9.8 m/s$^2$; and $\phi$ is the percentage of the volume of the cluster that is occupied by particles (volume fraction of the cluster).

Figure 20:
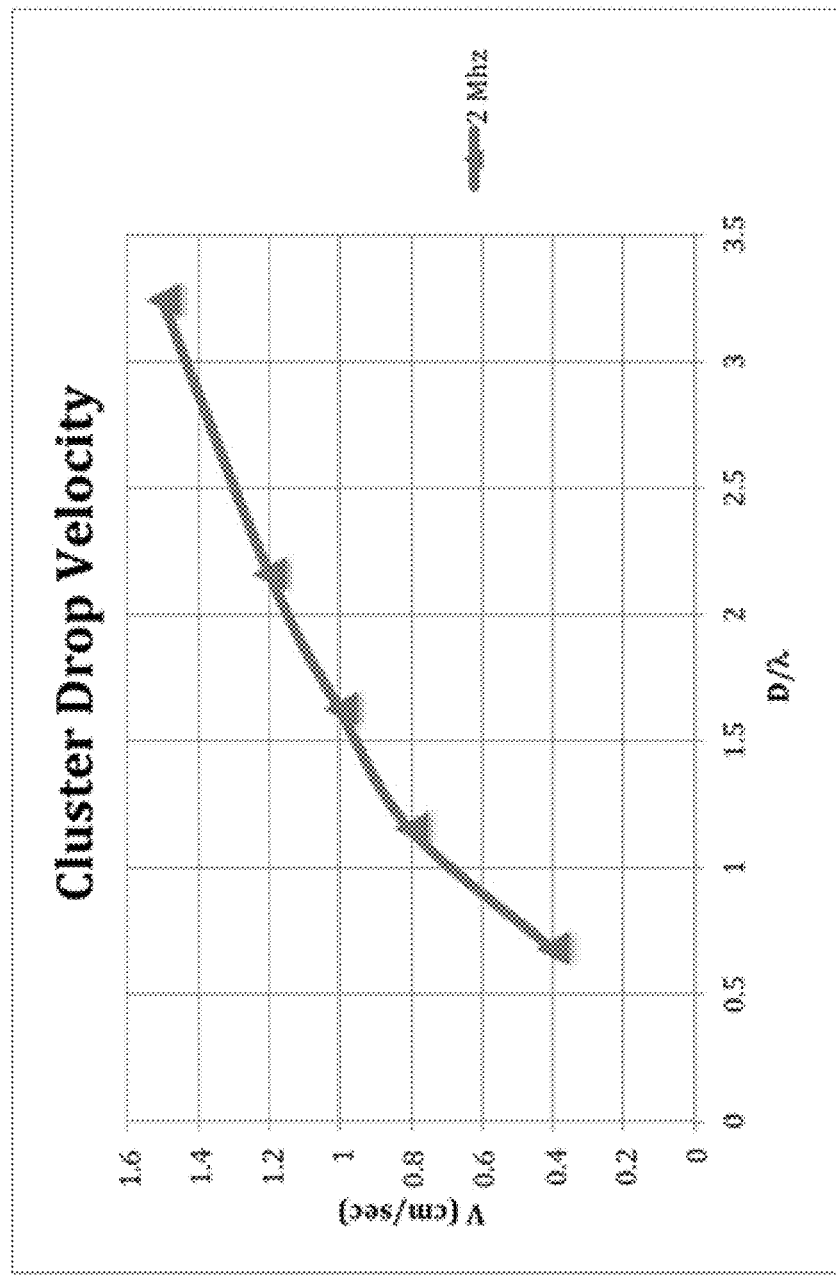
Figure 21:
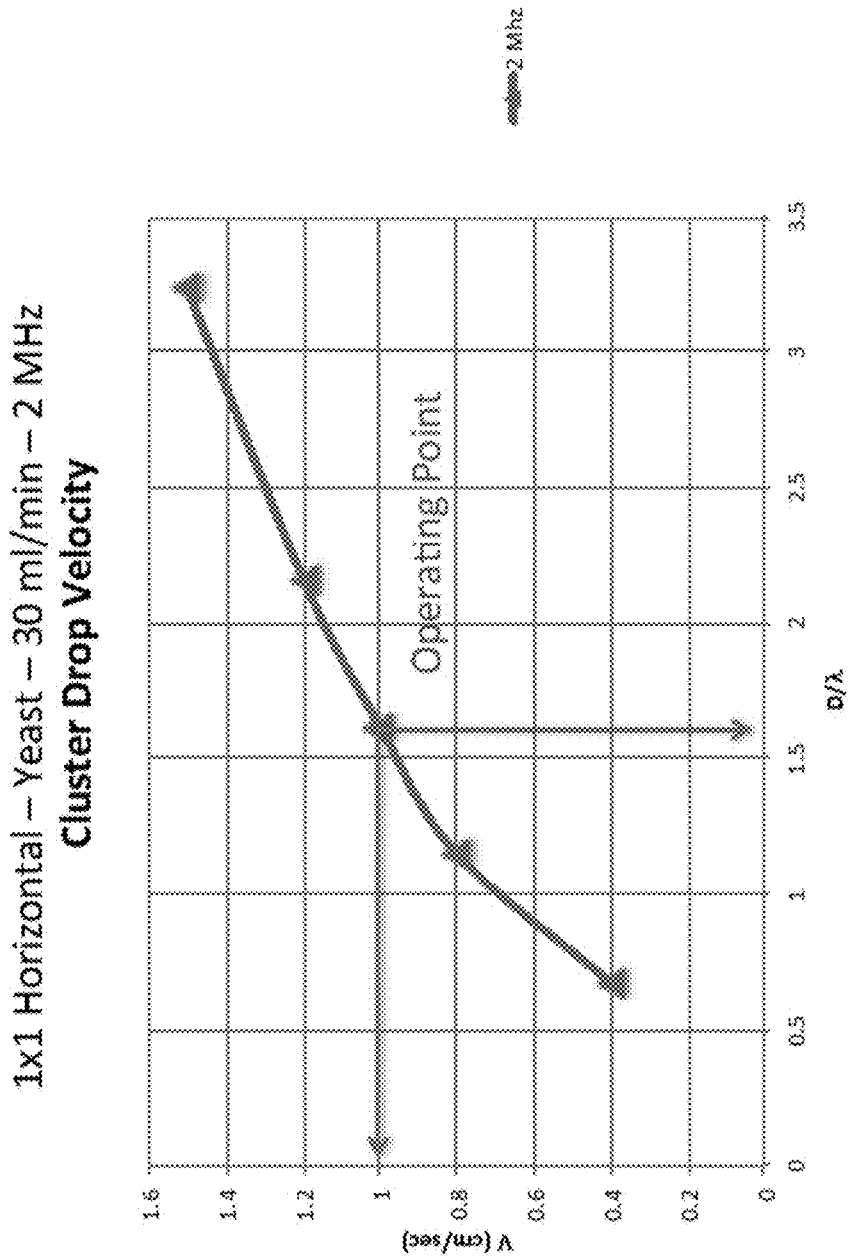
Figure 22:
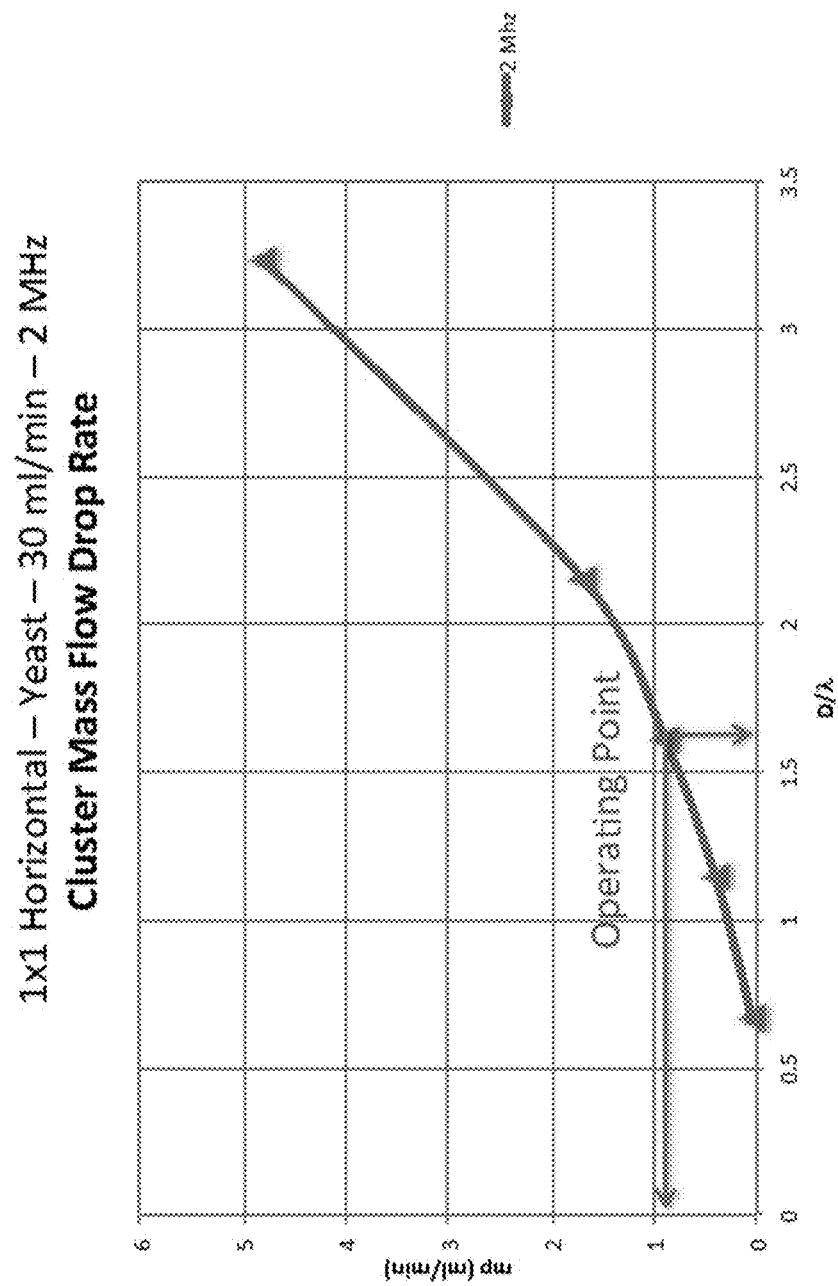
Figure 23:
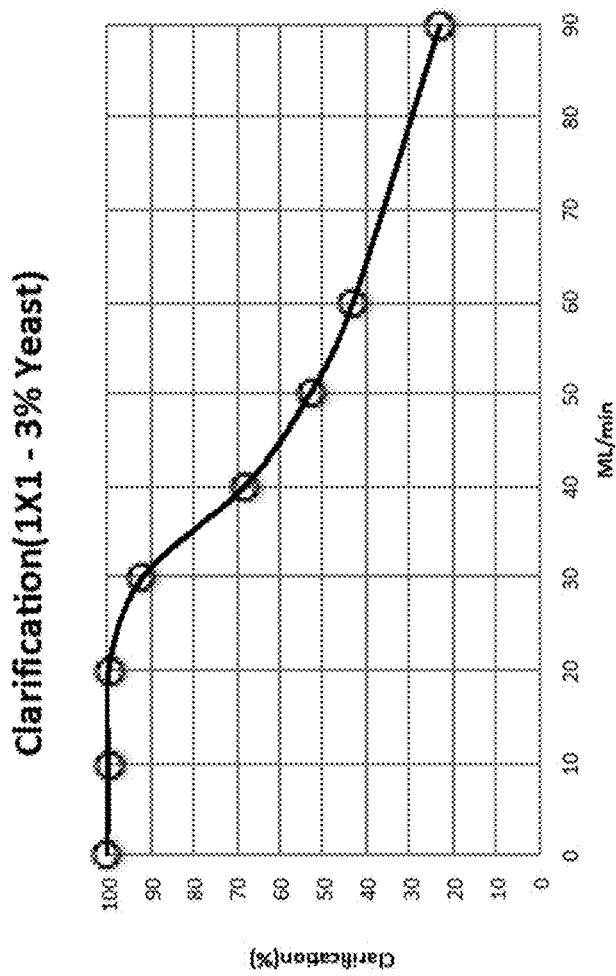
Figure 24:
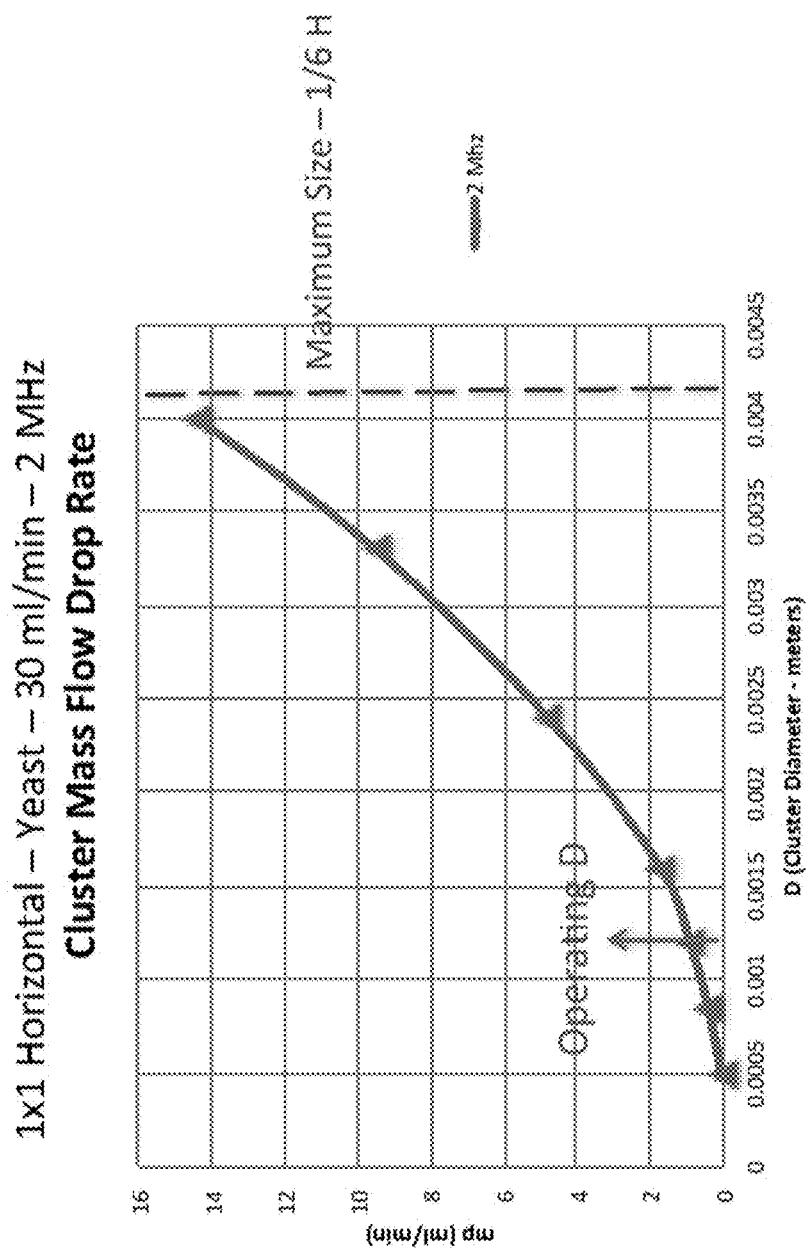
Figure 25:
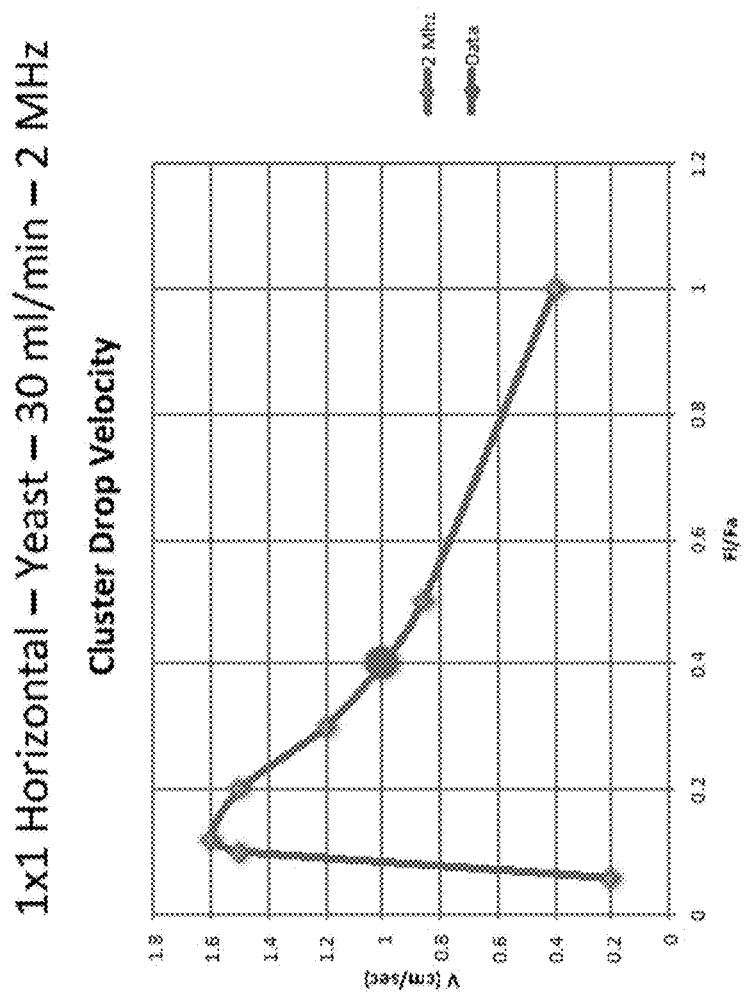
Figure 26:
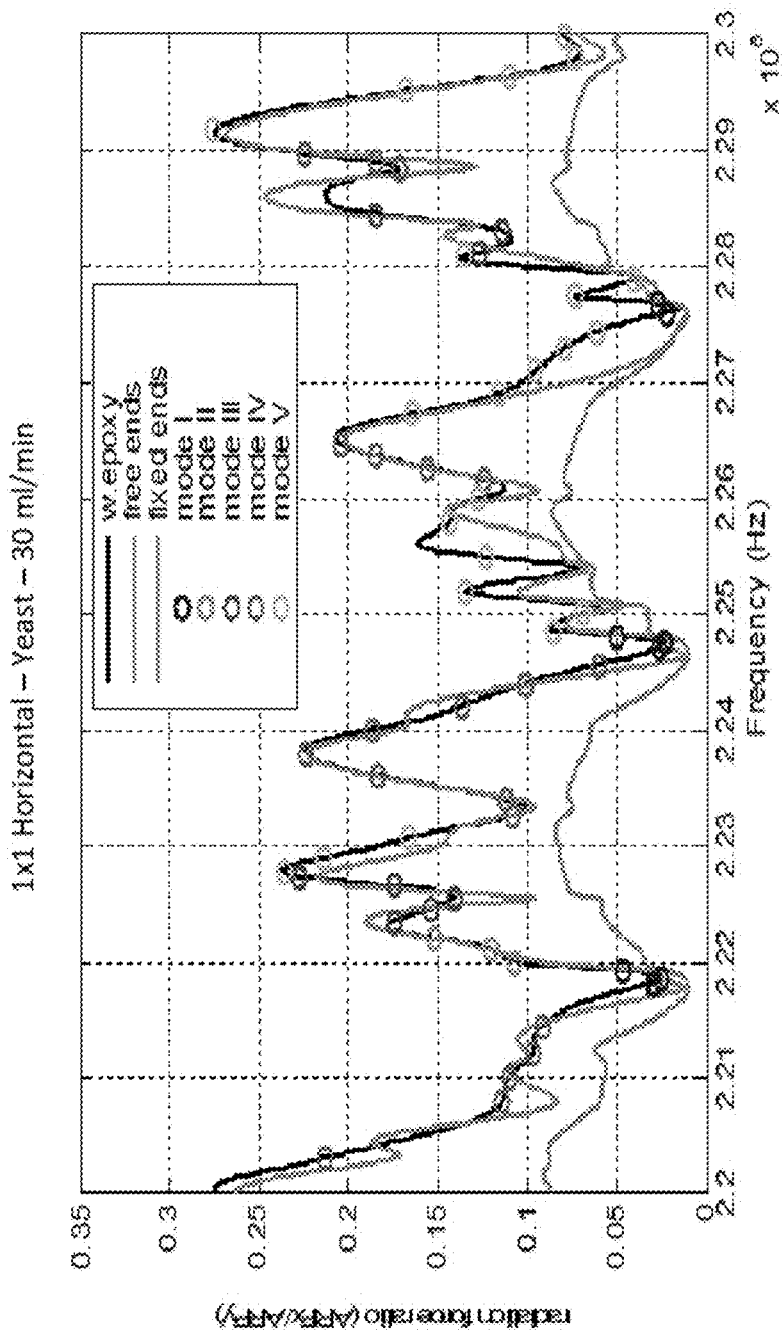

The equations can be solved to obtain estimated cluster drop velocity and collector effectiveness. FIG. 20 presents the predicted cylindrical cluster drop velocity as a function of non-dimensional cluster diameter (D/λ) where lambda (λ) is the axial wavelength of the standing wave (here 2 MHz). These results predict a significant increase in cluster drop out velocity with increase in cluster size. Larger clusters and higher drop velocities will result in more efficient particle collection. This means the system will separate and collect with higher concentrations, or at higher flowrates with the same concentration.

A functional representation of the important non-dimensional parameters of the physical process can be obtained as follows.

$$\frac{D}{\lambda} = f\left(R_{eD}, \frac{\rho_p}{\rho_f}, S, \frac{F_L}{F_A}, \frac{P}{\rho c^2}, \frac{h}{d}, \frac{P}{\rho V^2}\right)$$

where $R_{eD}$ is the Reynolds number; S is the acoustic contrast factor; $F_L$ is the lateral radiation force component; $F_A$ is the axial radiation force component; P is the acoustic pressure; V is the flow-through velocity of the particle/fluid mixture; and the other variables are as described above.

Non-dimensional parameters provide fewer and more universal variables for a given physical phenomenon. The cluster drop out size divided by the primary acoustic standing wavelength is seen to be a function of Reynolds number, density ratio, contrast factor, lateral to axial particle radiation force, acoustic pressure over speed of sound dynamic pressure, chamber dimension over particle diameter and acoustic pressure over fluid dynamic pressure. Reynolds number variations with different system operations are assumed small. For a fixed system, same mixture, same power input, and the same flowrate, the non-dimensional cluster drop out diameter can be determined experimentally.

The test illustrated in FIG. 15A was visually measured to determine the accuracy of the derived equations. Visual measurements of FIG. 15A indicated that D~0.0012 meters; V~0.01 m/s drop velocity; and λ~0.00074 meter wavelength, for a D/λ~1.62. According to the equations, with D/λ=1.62, the cylinder drop velocity is approximately 0.01 m/s, as indicated in FIG. 21. Also, the cylinder cluster diameter D=0.0012 meters, and the Reynolds number $R_{eD}$=15, which agrees with the experimentally measured values.

FIG. 22 is a graph of particle collection flowrate in ml/min versus cluster drop out diameter. These values were obtained assuming only the three bottom cylindrical clusters dropped, which was made because all other clusters were directly above the bottom row of clusters. That is, the top cluster will drop, hit the middle cluster location, drop, hit the bottom cluster location, and then drop out of the chamber and be collected. The same analysis can be carried out for higher order modes which give more number of clusters.

FIG. 23 is a graph showing the clarification performance of the system versus the cluster particle flowrate, using the cluster particle flowrate from FIG. 22. Again, the agreement with measured efficiency of the 1×1 system with yeast follows the analytical model. The model predicts good clarification up to a system flowrate of 30 mL/min. This is consistent with the measured yeast performance of the acoustophoretic separator.

FIG. 24 is a graph showing predicted system particle collection potential versus cluster diameter. These results show that cluster size is key to collection improvement. A larger cluster size allows faster dropout and faster clarification. Moreover, cluster size can be increased by lowering the standing wave frequency. This increases lambda, and therefore increases cluster diameter, D. It will also be shown that cluster size can be increased by decreasing the lateral acoustic radiation forces by operating the crystal using an operating frequency that has a lower multi-mode amplitude and a higher planar mode amplitude.

Next, an analytical model linking lateral-to-axial radiation force ratio (X) to particle cluster size (D) can be developed by assuming a constant pressure through the cluster:

$$\rho_A = \rho_F$$

(i.e., the dense mixture in the fluid acts as a stationary fluid), and $$\rho_A = \frac{F_A}{\pi D^2/4}$$

and $$\rho_F = \frac{xF_A}{D\lambda/2}$$

where the dominant forces generating the pressure are the lateral and axial forces on the particles in the cluster. Solving the above equations, the expression can be reduced to:

$$D/\lambda = 0.64/x$$

This expression indicates that the cluster diameter will increase inversely with the lateral to axial radiation force ratio. If the axial radiation force is fixed, the particle cluster diameter will increase with a decrease in the lateral radiation force. The effect is similar to pushing inwards on a balloon, where the balloon dimension will be larger perpendicular to the direction in which the push is applied.

FIG. 25 is a graph showing the predicted cluster drop velocity versus the lateral-to-axial radiation force ratio. The velocity is seen to increase dramatically with lower lateral forces, with a peak when $F_L/F_A$ is between 0.1 and 0.2. This is due to larger cluster diameters. The drop off in velocity at extremely low lateral forces is a result of the large cluster diameters interfering with each other and retarding collection. For the particle clusters to fall, there has to be room between them allowing clear fluid to flow upward (satisfying continuity). At x=0, the clusters would have infinite diameter, i.e. be a plane of particles rather than a cluster.

Particle drop out occurs when the cluster size reduces the acoustic radiation force per unit volume below the constant gravity force per unit volume of the cluster. The change in acoustic radiation force per unit volume of a cluster is directly determined by the spatial varying radiation force field. The gravity force field is constant. The size of the particle clusters formed will therefore be a function of the lateral radiation force generated on the particle clusters and the density of the particles. Lower density, for the same radiation force values, will result in larger clusters. The cluster sizes in the tests discussed above have generally used yeast. Macro-scale, ultrasonic separators are proposed for separating out various particle or cells from a mixture. Separating Chinese Hamster Ovary (CHO) cells from its protein solution is one of the more important proposed applications. CHO cells have slightly different radiation force values than yeast, but have a much lower density. Therefore, the particle cluster size for CHO to drop out is dramatically larger than for yeast. CHO cluster sizes can even be large enough for particle clusters to vertically attach and allow high concentration mixture to flow down to the collector.

The piezoelectric crystals of the transducers described herein can be operated at various modes of operation by changing the drive frequency exciting the crystal. Each operation point has an infinite number of vibration modes superimposed, but typically has one or more modes that are dominant. FIG. 26 presents COMSOL results for crystal vibration and lateral radiation forces on a typical particle size. The ratio of lateral to axial radiation force is plotted versus operating frequency. Points are labeled on the curve where a specific mode of vibration is dominant. Mode I represents the planar vibration mode of the crystal designed to generate a 2 MHz standing wave in a mixture. Mode III represents the 3×3 mode operation of a 1×1 crystal. These analytical results show that the 3×3 mode can be dominant with different levels of lateral radiation force. More specifically, operating the system at a frequency of 2.283 MHz will generate the lowest lateral force ratio of about 1.11 for a 3×3 mode. This will generate the largest cluster size and the best collection operation. Operating the devices and systems described herein at a frequency for a given system that produces a desired 3D mode with the lowest lateral force ratio is desirable to achieve the most efficient separation.

Figure 27:
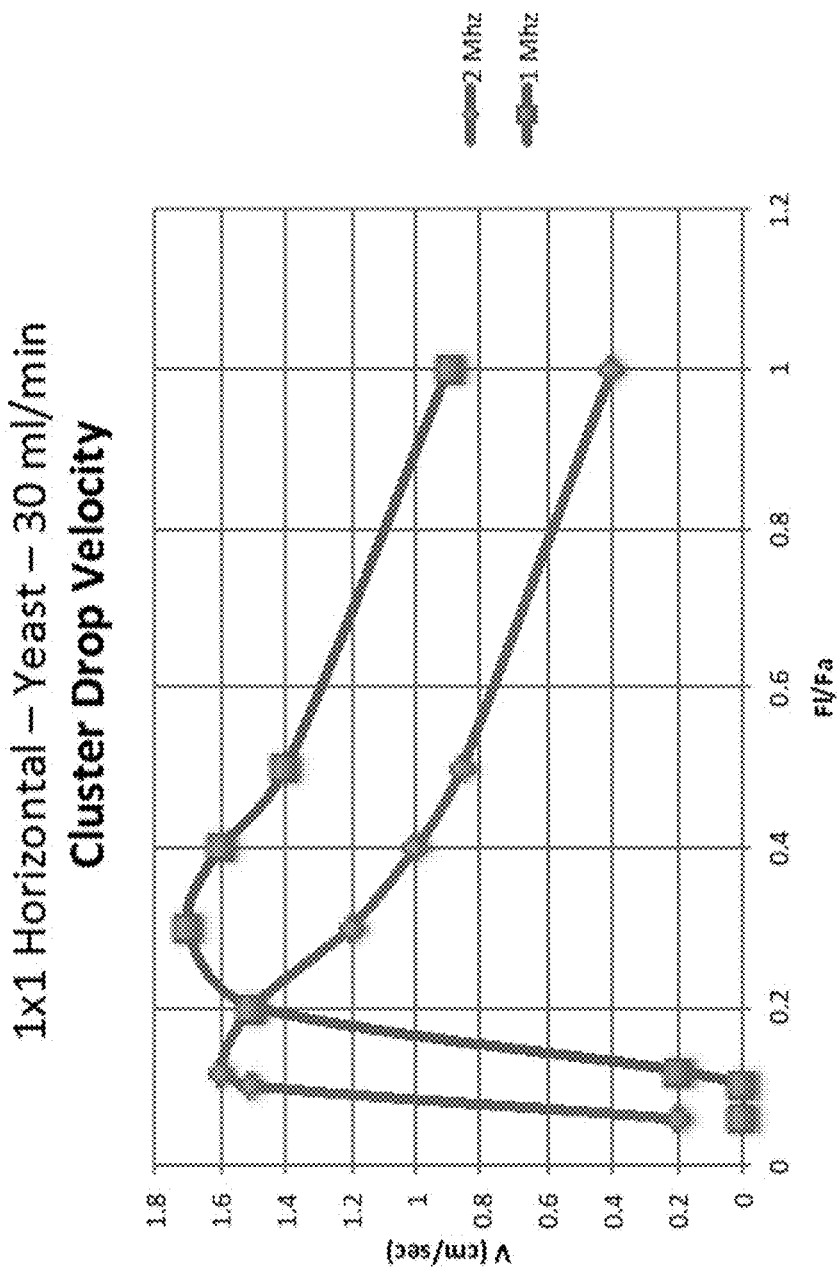
Figure 28:
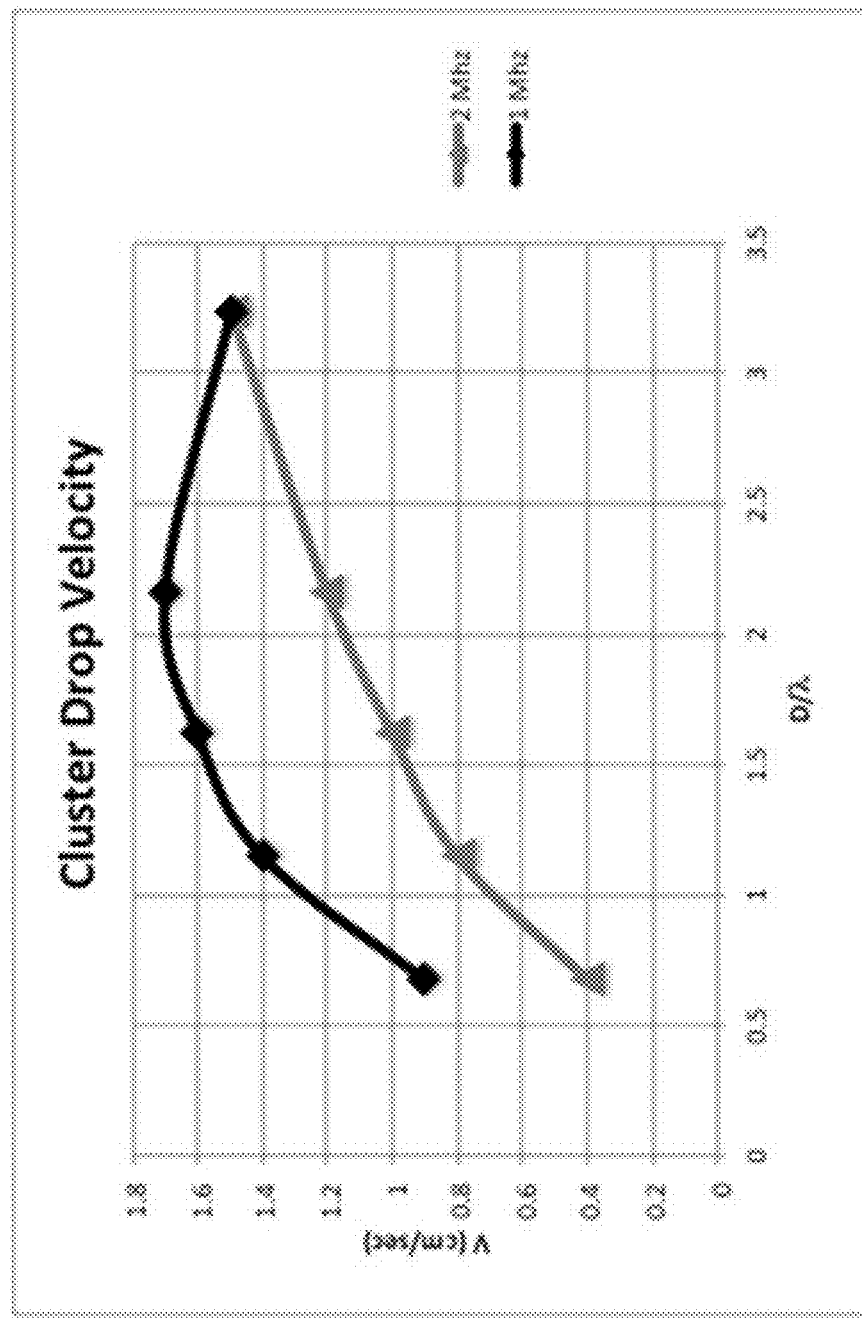
Figure 29:
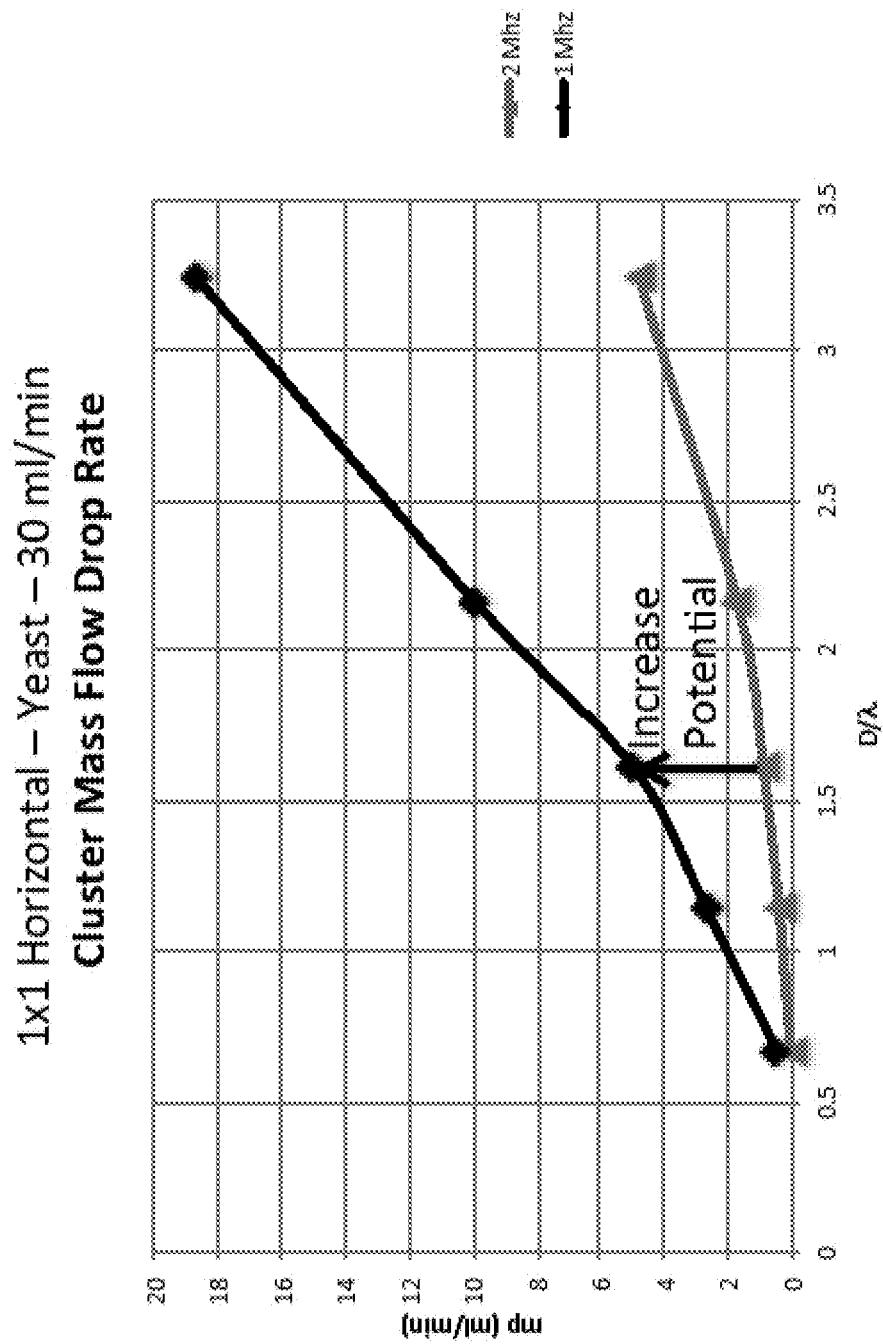

Cluster size can also be increased by lowering the standing wave frequency. This increases lambda, and therefore increases cluster diameter (D). FIG. 27 is a graph of predicted cluster drop velocity versus lateral-to-axial radiation force ratio for both 1 MHz and 2 MHz frequencies. These results show a significant increase in drop out velocity with the lower frequency, 1 MHz operation, with a peak between $F_L/F_A$ of 0.2 to 0.4. The increase in performance with lower frequency is a result of larger cluster diameters at all force ratios with the system operating at 1 MHz. This is verified in FIG. 28, which shows the cluster drop velocity versus the non-dimensional cluster diameter, and in FIG. 29, which shows the predicted particle collection rate versus non-dimensional cluster diameter. At a D/λ of 1.62, which represents the measured cluster diameter drop out size for yeast, operation at 1 MHz is seen to increase collection potential five times.

Figure 30:
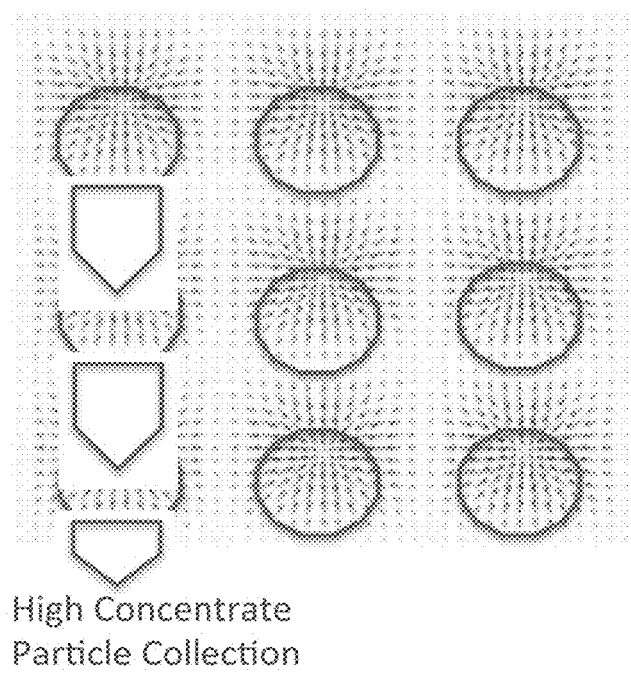
Figure 31:
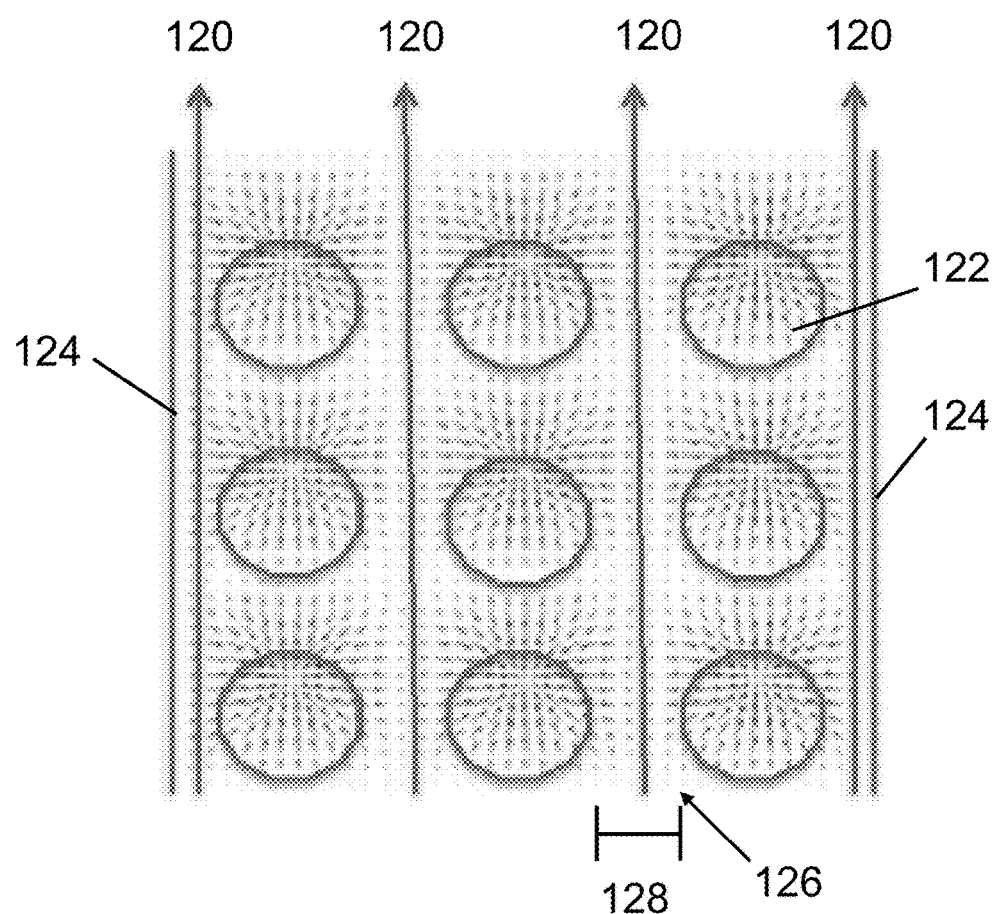

At lower frequencies, however, different phenomena begin to occur. It was previously mentioned above with respect to FIG. 16 that when the particle clusters fall, the fluid in the channels between clusters also falls and fluid flows around the clusters rather than through the channels. In FIG. 16, the frequency was 2 MHz. At a lower frequency of 1 MHz, the channels between the clusters doubles in size, so the fluid/particle mixture can being flowing between clusters. As a result, the particle clusters can grow without falling out. Rather, due to the distribution of the acoustic radiation force and gravity forces, there is a critical size where the cluster boundary intersects the downward particle radiation force region below the cluster (see prior discussion of FIG. 17). Particle clusters in trapping lines will begin to "bleed" into the trapping lines below them. This is depicted in FIG. 30. This type of action may also provide a benefit because only the particle clusters drop out, not the fluid between them, which can be considered an increase in the concentration of particles In addition, it is possible to obtain particle clusters that have large diameters but low density. For example, this can happen with CHO cells at both frequencies of 1 MHz and 2 MHz. With larger cluster diameters, the fluid/particle mixture flowing through and around the clusters will have a higher velocity, and it becomes possible for the fluid drag force to dominate, such that large particles will not drop out/rise out of the host fluid. This is depicted in FIG. 31. In this cross-sectional view, the fluid/particle mixture flows upward, as indicated by the arrows 120, through and around nine circular particle clusters 122 within an acoustic chamber marked by walls 124. The particle clusters indicate the position of the nine trapping lines within the acoustic chamber (see FIG. 14A). As illustrated here, the arrows illustrate fluid flow through relatively straight vertical channels 126 having a cross-sectional area indicated by reference numeral 128. Without being bound by theory, these "leakage pathways" result in little to no lateral forces being exerted on the large particle clusters, so that they do not drop out/rise out.

Figure 32B:
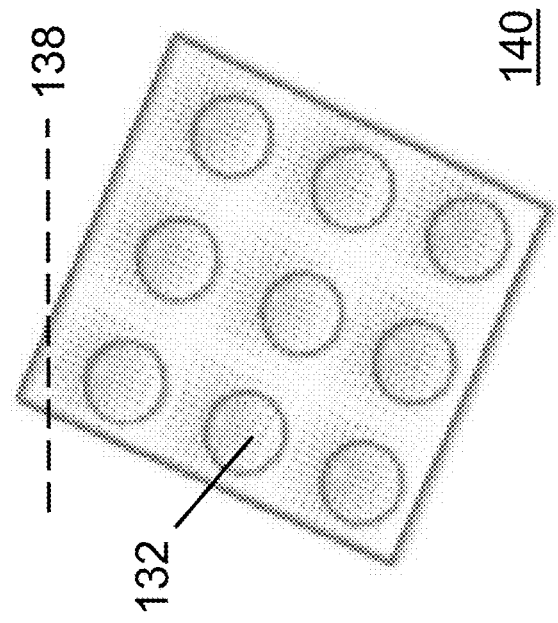
Figure 32A:
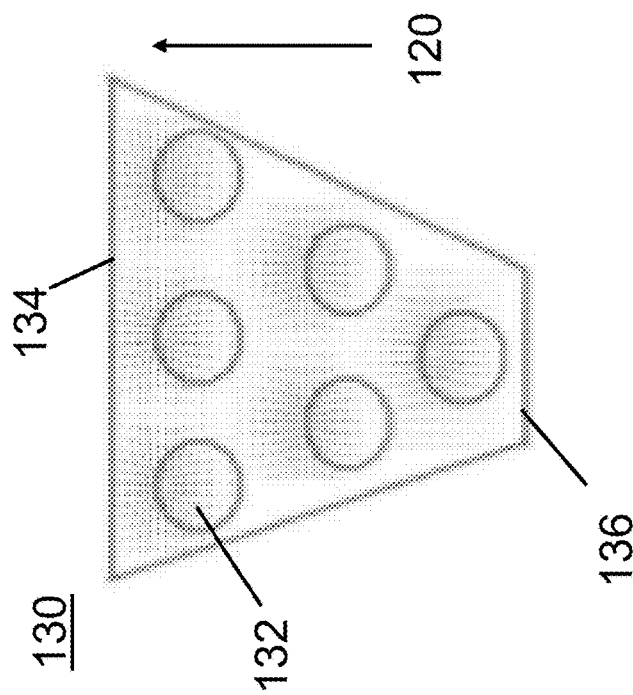

A solution to this problem is to orient the transducer to that the trapping lines produced thereby minimize the cross-sectional area for straight vertical channels between the trapping lines. This is ideally achieved by placing the trapping lines such that no two trapping lines are located vertically above each other. Two potential configurations are illustrated in FIG. 32A and FIG. 32B. In FIG. 32A, the transducer 130 has an irregular perimeter with four sides, i.e. is an irregular polygon. This transducer can be operated in a mode that generates six sets of trapping lines 132, with sides 134, 136 indicating a horizontal plane. Fluid flow is indicated by vertical arrow 120, which is normal to the horizontal plane. As can be seen here, there is very little vertical cross-sectional area for a straight vertical channel. Similarly, in FIG. 32B, dashed line 138 indicates a horizontal plane, and there is very little vertical cross-sectional area for a straight vertical channel. Here, the transducer is a square transducer 140 with nine trapping lines 132 as depicted in FIG. 14A, but tilted. Rather, in these two figures, fluid flow is circuitous, which reduces the upward fluid drag force, permitting particle clusters to eventually drop out.

Figure 33:
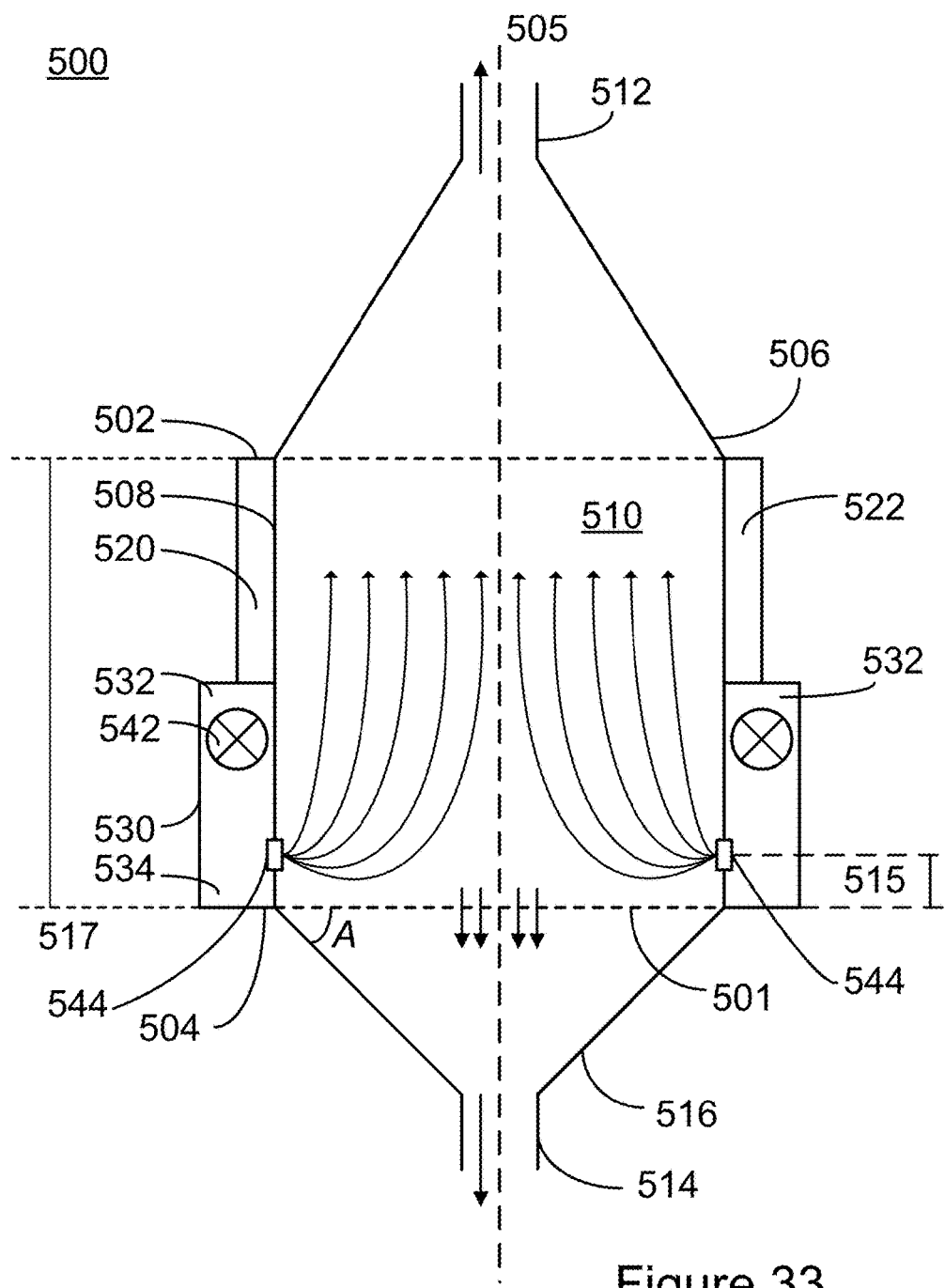

FIG. 33 is a cross-sectional diagram of a configuration for an acoustophoretic device in which the methods of the present disclosure can be used. This device includes dump diffusers at the inlet(s) that create a more uniform flow through the device. The device 500 has a vertical orientation, with an upper end 502 and a lower end 504. The device also has two dump inlets and a collector design which provides a vertical plane or line of symmetry 505. Generally, the cross-section of the device in the flow direction is circular or rectangular. The device is formed from a housing 506 having a sidewall 508 that defines an acoustic chamber 510 therein. The acoustic chamber is empty, i.e. there is nothing within the chamber, and fluid flows through the acoustic chamber. At least one upper outlet 512 is present at the upper end of the acoustic chamber 510. At least one lower outlet 514 is present at the lower end 504 of the acoustic chamber. A shallow wall 516 is present at the lower end of the acoustic chamber, and leads to the outlet 514. The shallow wall has a shallow angle when measured relative to a horizontal plane (denoted here by the chamber bottom, line 501), with the angle A being in embodiments about 60° or less, including about 30° to about 45°. At least one ultrasonic transducer 520 is present on the sidewall 508, and at least one reflector 522 is present on the sidewall 508 opposite the ultrasonic transducer 520. The transducer 520 and the reflector 522 are located closer to the upper end 502 of the device.

This device 500 also includes a symmetrical, dual dump diffuser, plenum inlet configuration. Here, two dump diffusers 530 are placed on opposite sides of the device. Each dump diffuser has an upper end 532 and a lower end 534. An inlet 542 is located at the upper end 532, and at least one diffuser outlet 544 is located at the lower end. These diffuser outlets 544 also pass through the sidewall 508, and can be considered as diffuser inlets into the acoustic chamber. The diffuser outlet(s) can be in the form of a slot or a line of holes, and they are placed above the bottom of the acoustic chamber. In embodiments, the diffuser outlets are located above the chamber bottom 501 at a height 515 that is between 5% and 100% of the height 517 of the acoustic chamber, and more particularly between 5% and 25% of the height of the acoustic chamber. The diffuser outlets 544 provide a flow direction parallel to the axial direction of the acoustic standing waves generated by the ultrasonic transducer. The diffuser outlets are also arranged so that they are in opposing locations, so that the horizontal velocity will decrease to zero in the center of the acoustic chamber.

Each dump diffuser includes an entrance port 542 into which the mixture of host fluid/second fluid or particulate flows (the X refers to the flow direction into the paper). This eliminates downward flow in the acoustic chamber. The mixture fills up the chamber in the dump diffuser and then flows horizontally out of the diffuser outlet(s) 544 and enters the acoustic chamber, where the mixture flows vertically upwards and out of the upper outlet 512. The dump diffuser reduces/eliminates flow pulsations and flow non-uniformities that result from a horizontal inlet flow where gravity effects dominate. The diffuser outlets 544 then bring the heavier mixture into the acoustic chamber above the bottom of the chamber (line 501) and below the ultrasonic transducer and the nodal clusters that form in the ultrasonic standing waves. This minimizes any disturbances of the clusters set up by inflowing material.

The vertical plane or line of symmetry 505 is aligned with gravity forces. Also shown are flow streamlines which are desirably symmetrical, since this minimizes non-uniformities, eddy disturbances, circulation, and disturbance of clusters falling through outlet 514 to be collected. Symmetry also maximizes gravity forces in the inlet flow distribution and particle collection process. Because it is heavier than the permeate exiting at the top of the device, the (relatively) heavy incoming mixture comes in near the bottom of the acoustic chamber. The symmetrical inlets also assure that the incoming mixture spreads out across the bottom of the chamber due to gravity forces, and provides near uniform velocity profiles from bottom to top. The horizontal velocity of the mixture will decrease to zero as it approaches the center of the acoustic chamber due to the dual opposing inlet flows. A uniform velocity provides the best separation and collection results because the lateral acoustic forces have to overcome particle drag for the clusters to grow and continuously drop out of the acoustic chamber. This also eliminates the need for an inlet flow distributor.

As the particle clusters drop out, the axial acoustic forces associated with the standing wave will keep the clusters intact. This assures rapid dropping of the clusters with high terminal velocities, on the order of 1 cm/sec. This is extremely fast compared to the chamber flow velocities, which are on the order of 0.1 cm/sec to 0.3 cm/sec. The shallow wall angle means the cylindrical particle clusters have to drop only a very short distance before they exit the acoustic chamber, so that little dispersion of the clusters occurs. Ideally, the system operates with 3 to 12 trapping lines per square inch of transducer. The symmetry, minimum flow disturbance in the central collection region, and shallow collector walls provide good collection without the need for baffles/laminar plates.

Figure 34:
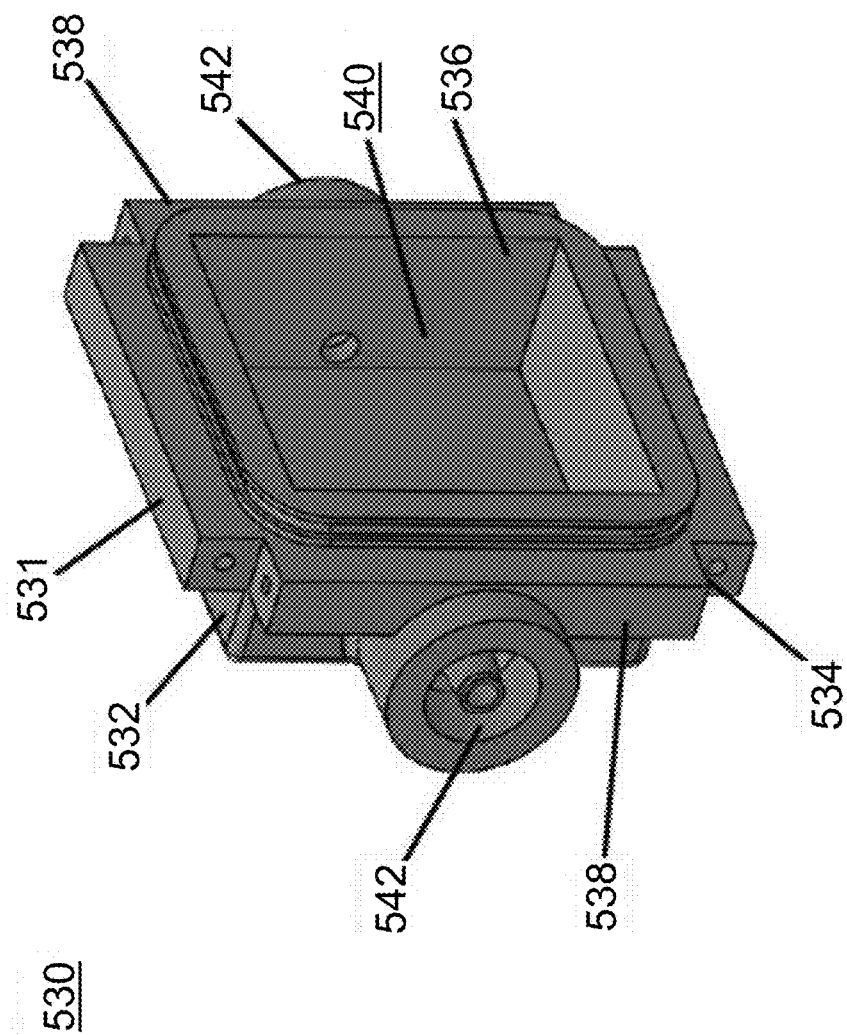
Figure 35:
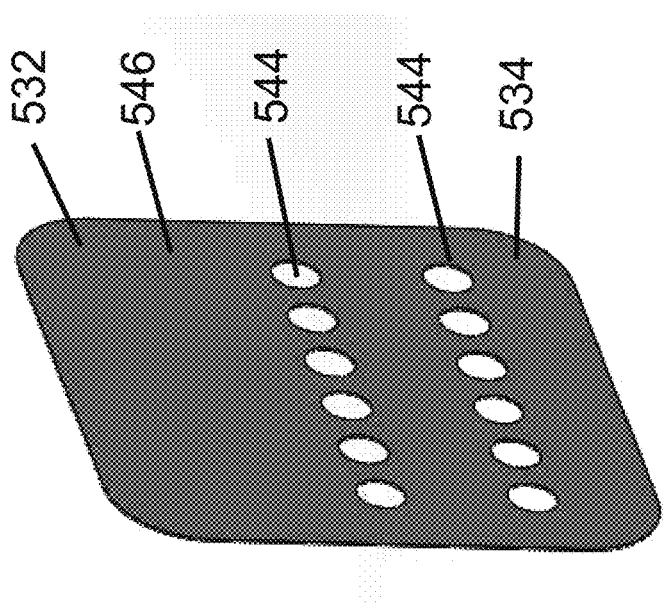

FIG. 34 and FIG. 35 provide additional detail on the dump diffusers that are used for providing a more uniform flow of the mixture of host fluid and particulate into the acoustic chamber 510. FIG. 34 is a perspective view with the front plate removed, showing both the interior and the exterior of a dump diffuser. FIG. 35 is a perspective view of the front plate of the dump diffuser. Starting with FIG. 34, the dump diffuser 530 includes a housing 531 having an upper end 532, an opposite lower end 534, two side faces 538, and a front face 536. A hollow chamber 540 is present within the housing 531. The dump diffuser also includes an entrance port 542 that receives the mixture and leads into the chamber 540. The entrance port 542 is present on the upper end and on a side face 538 of the housing; two entrance ports are visible here. FIG. 35 is a picture of the front plate 546 which is attached to the front face 536 of the housing. As illustrated here, the outlet 544 is located on the lower end 534 and is in the form of two lines of holes, though these could also be in the form of a thin slot. In use, the mixture of host fluid/second fluid or particulate enters through entrance ports 542 and fills up the chamber 540. Pressure then pushes the mixture uniformly out through outlets 544.

One specific application for the acoustophoresis devices and methods disclosed herein is in the processing of bioreactor materials. It is important to be able to filter all of the cells and cell debris from the expressed materials that are in the fluid stream. The expressed materials are composed of biomolecules such as recombinant proteins or monoclonal antibodies, and are the desired product to be recovered. Through the use of acoustophoresis, the separation of the cells and cell debris is very efficient and leads to very little loss of the expressed materials. This is an improvement over current filtration processes (depth filtration, tangential flow filtration, and the like), which show limited efficiencies at high cell densities, so that the loss of the expressed materials in the filter beds themselves can be up to 5% of the materials produced by the bioreactor. The use of mammalian cell cultures including Chinese hamster ovary (CHO), NS0 hybridoma cells, baby hamster kidney (BHK) cells, and human cells has proven to be a very efficacious way of producing/expressing the recombinant proteins and monoclonal antibodies required of today's pharmaceuticals. The filtration of the mammalian cells and the mammalian cell debris through acoustophoresis aids in greatly increasing the yield of the bioreactor. The acoustophoresis process, through the use of multidimensional acoustic waves, may also be coupled with a standard filtration process upstream or downstream, such as depth filtration using diatomaceous earth, tangential flow filtration (TFF), or other physical filtration processes.

Desirably, flow rates through the devices of the present disclosure can be a minimum of 4.65 mL/min per $cm^2$ of cross-sectional area of the acoustic chamber. Even more desirably, the flow rate can be as high as 25 mL/min/$cm^2$, and can range as high as 40 mL/min/$cm^2$ to 270 mL/min/$cm^2$, or even higher. This is true for batch reactors, fed-batch bioreactors and perfusion bioreactors.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A method of separating a host fluid from a second fluid or particulate, the method comprising:
    flowing a mixture of the host fluid and the second fluid or particulate through an acoustophoresis device, the device comprising:
        a housing having a sidewall that defines an acoustic chamber;
        at least one outlet from the acoustic chamber;

at least one inlet to the acoustic chamber; and at least one ultrasonic transducer located on the sidewall of the acoustic chamber and at least one reflector located on the sidewall of the housing opposite the at least one ultrasonic transducer, the transducer including a piezoelectric material driven by a voltage signal to create a multi-dimensional acoustic standing wave in the acoustic chamber; and trapping smaller particles of the second fluid or particulate in the acoustic standing wave to generate particle clusters that subsequently fall into or rise into the least one outlet;

wherein the acoustic standing wave has a lateral radiation force and a axial radiation force that are of the same order of magnitude.

2. The method of claim 1, wherein the piezoelectric material is in the shape of an irregular polygon.

3. The method of claim 1, wherein the piezoelectric material is operated to produce a set of vertically-staggered trapping lines.

4. The method of claim 1, wherein the at least one ultrasonic transducer is driven at a frequency of about 0.5 MHz to about 4 MHz.

5. The method of claim 1, wherein the at least one inlet is part of a dump diffuser.

6. The method of claim 1, wherein the at least one inlet is located at a height between 5% and 75% of a height of the acoustic chamber.

7. The method of claim 1, wherein the at least one inlet is in the shape of holes or slots that provide an initial flow direction parallel to the multi-dimensional acoustic standing wave generated by the at least one ultrasonic transducer.

8. The method of claim 1, wherein the device includes a shallow wall below the at least one inlet and leading to the at least one outlet, wherein the shallow wall has an angle of 60° or less relative to a horizontal plane.

9. The method of claim 1, wherein a ratio of the lateral radiation force to the axial radiation force is about 0.5 or less.

10. The method of claim 1, wherein the at least one inlet includes a plurality of inlets located about the housing, such that the inflow of the mixture into the acoustic chamber is uniform and symmetrical.

11. The method of claim 1, wherein the piezoelectric material is oriented to minimize cross-sectional area for straight vertical channels between trapping lines generated by the acoustic standing wave.

12. The method of claim 1, wherein the mixture of the host fluid and the second fluid or particulate is flowed through the acoustophoresis device at a rate of at least 4.65 mL/minute per cm².

13. The method of claim 1, wherein the particulate is Chinese hamster ovary (CHO) cells, NS0 hybridoma cells, baby hamster kidney (BHK) cells, human cells, T cells, B cells, NK cells, algae, bacteria, viruses, or microcarriers.

14. A method of separating a host fluid from a second fluid or particulate, the method comprising:

flowing a mixture of the host fluid and the second fluid or particulate through an acoustophoresis device, the device comprising:
a housing that includes an acoustic chamber;
at least one ultrasonic transducer located on a wall of the acoustic chamber and at least one reflector located on the wall of the housing opposite the at least one ultrasonic transducer, the transducer including a piezoelectric material driven by a voltage signal to create a multi-dimensional acoustic standing wave in the acoustic chamber, resulting in a set of trapping lines in the acoustic chamber, the transducer being oriented to minimize cross-sectional area for straight vertical channels between the trapping lines; and capturing smaller particles of the second fluid or particulate in the trapping lines to cluster and continuously gravity separate the second fluid or particulate from the host fluid.

15. The method of claim 14, wherein the at least one ultrasonic transducer is driven at or below a frequency of about 1.5 MHz.

16. The method of claim 14, wherein the mixture enters the acoustic chamber through at least one inlet that is part of a dump diffuser.

17. The method of claim 16, wherein the at least one inlet is located at a height between 5% and 75% of a height of the acoustic chamber.

18. The method of claim 16, wherein the at least one inlet includes a plurality of inlets located about the housing, such that the inflow of the mixture into the acoustic chamber is uniform and symmetrical.

19. The method of claim 14, wherein the acoustophoresis device is reflectionally symmetrical through a vertical plane.

20. The method of claim 14, wherein the particulate is Chinese hamster ovary (CHO) cells, NS0 hybridoma cells, baby hamster kidney (BHK) cells, human cells, T cells, B cells, NK cells, algae, bacteria, viruses, or microcarriers.

* * * * *